US009795753B2

(12) United States Patent
Qiu

(10) Patent No.: US 9,795,753 B2
(45) Date of Patent: Oct. 24, 2017

(54) INTUBATION DELIVERY SYSTEMS AND METHODS

(76) Inventor: Chunyuan Qiu, Huntington Beach, CA (US)

(*) Notice: Subject to any disclaimer, the term of this patent is extended or adjusted under 35 U.S.C. 154(b) by 1091 days.

(21) Appl. No.: 13/414,590

(22) Filed: Mar. 7, 2012

(65) Prior Publication Data

US 2013/0237763 A1  Sep. 12, 2013

Related U.S. Application Data

(63) Continuation-in-part of application No. 12/764,804, filed on Apr. 21, 2012, now Pat. No. 8,894,569.

(51) Int. Cl.
*A61M 16/04* (2006.01)
*A61B 1/267* (2006.01)
*A61M 16/00* (2006.01)
*A61B 1/00* (2006.01)

(52) U.S. Cl.
CPC ..... *A61M 16/0495* (2014.02); *A61B 1/00052* (2013.01); *A61B 1/267* (2013.01); *A61M 16/0488* (2013.01); *A61B 1/00048* (2013.01); *A61B 1/00105* (2013.01); *A61M 2016/0027* (2013.01); *A61M 2016/0036* (2013.01); *A61M 2016/0413* (2013.01); *A61M 2205/3368* (2013.01); *A61M 2205/3375* (2013.01); *A61M 2205/584* (2013.01); *A61M 2230/437* (2013.01)

(58) Field of Classification Search
USPC .................. 600/185, 188, 193, 194
See application file for complete search history.

(56) References Cited

U.S. PATENT DOCUMENTS 3,943,920 A * 3/1976 Kandel ............... 600/190
4,292,961 A   10/1981 Kawashima
4,366,810 A    1/1983 Slanetz, Jr.
(Continued)

FOREIGN PATENT DOCUMENTS

EP       0230790 A2   8/1987
WO     99/34726 A1   7/1999
(Continued)

OTHER PUBLICATIONS

ISA Patent Cooperation Treaty. International Search Report of PCT/US2008/073176. Nov. 14, 2008. 2 pages.
(Continued)

*Primary Examiner* — Nicholas Woodall
(74) *Attorney, Agent, or Firm* — McCoy Russell LLP

(57) ABSTRACT

Various methods and systems for delivery of an ETT for intubation are provided. In one example, an ETT delivery system includes a rail system for guiding insertion of an ETT and at least partially defining the motion of the ETT. The ETT delivery system further may include a video laryngoscope blade coupled to the rail system and a delivery mechanism. In some examples, the ETT delivery system further includes a positioner configured to adjust the motion of the ETT. As a further example, the ETT delivery system may include a swing arm and a guide rail to at least partially define the motion of the swing arm. Further, a drive-down mechanism may effect motion of the swing arm. As another embodiment, a rail system, a disposable blade and a positioner may be provided. Further, a delivery mechanism may be operatively linked with the integrated rail system.

11 Claims, 12 Drawing Sheets

(56) References Cited

U.S. PATENT DOCUMENTS

| | | | |
|---|---|---|---|
| 4,437,458 A * | 3/1984 | Upsher | 600/193 |
| 4,469,091 A | 9/1984 | Slanetz, Jr. | |
| 4,553,540 A * | 11/1985 | Straith | A61M 16/0488 |
| | | | 128/200.26 |
| 5,184,603 A * | 2/1993 | Stone | 600/193 |
| 5,257,636 A | 11/1993 | White | |
| 5,285,778 A | 2/1994 | Mackin | |
| 5,349,943 A * | 9/1994 | Ruiz | A61B 1/267 |
| | | | 600/189 |
| 5,445,161 A | 8/1995 | Huang | |
| 5,492,131 A | 2/1996 | Galel | |
| 5,498,231 A * | 3/1996 | Franicevic | A61B 1/267 |
| | | | 128/200.26 |
| 5,560,351 A | 10/1996 | Gravenstein et al. | |
| 5,591,130 A | 1/1997 | Denton | |
| 5,776,052 A * | 7/1998 | Callahan | A61B 1/267 |
| | | | 600/194 |
| 5,845,634 A * | 12/1998 | Parker | 128/200.26 |
| 5,951,461 A | 9/1999 | Nyo et al. | |
| 6,063,093 A | 5/2000 | Winston et al. | |
| 6,149,603 A | 11/2000 | Parker | |
| 6,161,537 A | 12/2000 | Gravenstein et al. | |
| 6,164,277 A | 12/2000 | Meridith | |
| 6,203,493 B1 | 3/2001 | Ben-Haim | |
| 6,349,720 B1 | 2/2002 | Clark | |
| 6,463,313 B1 | 10/2002 | Winston et al. | |
| 6,468,203 B2 | 10/2002 | Belson | |
| 6,659,962 B2 | 12/2003 | Ricciardelli | |
| 6,705,320 B1 | 3/2004 | Anderson | |
| 6,715,491 B2 | 4/2004 | Cooper et al. | |
| 6,757,557 B1 | 6/2004 | Bladen et al. | |
| 6,820,614 B2 | 11/2004 | Bonutti | |
| 6,858,005 B2 | 2/2005 | Ohline et al. | |
| 6,860,264 B2 | 3/2005 | Christopher | |
| 6,869,396 B2 | 3/2005 | Belson | |
| 6,890,297 B2 | 5/2005 | Belson | |
| 6,926,709 B2 | 8/2005 | Bieger et al. | |
| 6,970,732 B2 | 11/2005 | Winston et al. | |
| 6,981,947 B2 | 1/2006 | Melker | |
| 7,044,907 B2 | 5/2006 | Belson | |
| 7,087,013 B2 | 8/2006 | Belson et al. | |
| 7,089,928 B2 | 8/2006 | Besharim et al. | |
| 7,153,260 B1 * | 12/2006 | Girgis | 600/196 |
| 7,174,202 B2 | 2/2007 | Bladen et al. | |
| 7,178,519 B2 | 2/2007 | Melker et al. | |
| 7,182,728 B2 | 2/2007 | Cubb et al. | |
| 7,194,296 B2 | 3/2007 | Frantz et al. | |
| 8,652,033 B2 * | 2/2014 | Berci et al. | 600/199 |
| 2002/0074002 A1 | 6/2002 | Tung et al. | |
| 2002/0173799 A1 | 11/2002 | Besharim et al. | |
| 2003/0018276 A1 | 1/2003 | Mansy et al. | |
| 2003/0034035 A1 | 2/2003 | Raphael | |
| 2003/0092967 A1 * | 5/2003 | Fourie et al. | 600/191 |
| 2004/0039252 A1 | 2/2004 | Koch, III | |
| 2004/0199053 A1 | 10/2004 | Boulais et al. | |
| 2005/0076914 A1 | 4/2005 | Besharim et al. | |
| 2005/0107669 A1 | 5/2005 | Couvillon, Jr. | |
| 2005/0154261 A1 | 7/2005 | Ohline et al. | |
| 2005/0187434 A1 | 8/2005 | Dey et al. | |
| 2005/0209509 A1 | 9/2005 | Belson | |
| 2006/0004258 A1 | 1/2006 | Sun et al. | |
| 2006/0004260 A1 | 1/2006 | Boedecker et al. | |
| 2006/0122460 A1 | 6/2006 | Kamali | |
| 2006/0129055 A1 | 6/2006 | Orr et al. | |
| 2006/0180155 A1 | 8/2006 | Glassenberg et al. | |
| 2006/0201517 A1 | 9/2006 | Rich et al. | |
| 2007/0015967 A1 | 1/2007 | Boulais et al. | |
| 2007/0049794 A1 * | 3/2007 | Glassenberg | A61B 1/00032 |
| | | | 600/109 |
| 2007/0106117 A1 | 5/2007 | Yokota | |
| 2007/0106121 A1 | 5/2007 | Yokota et al. | |
| 2007/0106122 A1 | 5/2007 | Yokota et al. | |
| 2007/0129603 A1 | 6/2007 | Hirsh | |
| 2009/0044799 A1 | 2/2009 | Qiu | |
| 2010/0288272 A1 * | 11/2010 | Yokota | A61M 16/0488 |
| | | | 128/200.26 |

FOREIGN PATENT DOCUMENTS

| | | |
|---|---|---|
| WO | 2004/000107 A2 | 12/2003 |
| WO | 2009/023779 A1 | 2/2009 |

OTHER PUBLICATIONS

"Karl Storz Endoscopy-America, Inc." <http://www.anesthesiologynews.com/ancp/0808/content/ancp0808_042a.html?pagename=karl_storz_corporate_profile>, 2 pages. Accessed Dec. 4, 2009.

Wagner, Jason. "The Storz Video Laryngoscope." <http://www.epmonthly.com/subspecialties/technology/the-storz-video-laryngoscope/>, 3 pages. Accessed Dec. 4, 2009.

* cited by examiner

INTUBATION DELIVERY SYSTEMS AND METHODS

CROSS REFERENCE TO RELATED APPLICATIONS

The present application is a continuation-in-part of U.S. patent application Ser. No. 12/764,804, filed Apr. 21, 2010, and titled SYSTEMS AND METHODS FOR INTUBATION, the entire contents of which are incorporated herein by reference for all purposes.

BACKGROUND

Some medical procedures are invasive and potentially dangerous although they are necessary life-saving procedures. Intubation, specifically tracheal intubation, is typically performed at various medical conditions, such as application of general anesthesia, comatose, etc. Tracheal intubation involves the placement or the insertion of an endotracheal tube (ETT) into a patient's trachea to protect the patient's airway and provide a means of mechanical ventilation. Delay and/or misplacement of the endotracheal tube, such as misplacement of the endotracheal tube into esophagus, may cause permanent neurological damage or death. Malposition of the ETT may jeopardize airway protection or cause inadequate ventilation. It is therefore imperative to intubate a patient quickly and position the ETT correctly when a medical condition arises.

Various technologies have been developed to assist the placement of the endotracheal tube into the trachea, such as direct layrngoscopy, which utilize a laryngoscope during manual endotracheal tube insertion. Despite the improved visibility by various techniques and extensive training, failed intubation occurs frequently. While intubation is frequently performed by highly trained medical professionals in a hospital setting, such as an emergency room, operation room, or intensive care unit, etc., it is also performed by paramedics or equivalent in non-hospital settings, such as battlefields, motor vehicle accident scenes, or various field medical emergencies. Lack of experienced medical professionals and lack of easily-operated intubation devices may make the life-saving procedure difficult with potential loss of life in both hospital settings and non-hospital settings.

SUMMARY

The inventor herein has recognized that it may be desirable to have an easily operated intubation device that can intubate a patient without solely depending on manual guidance of the endotracheal tube. Embodiments are disclosed that relate to an intubation device comprising a rail system. In one example embodiment, an ETT delivery system is disclosed. In one example, an ETT delivery system includes a rail system defining an ETT delivery path for guiding insertion of an ETT and configured to at least partially define the motion of the ETT. The ETT delivery system further includes a positioner configured to adjust the motion of the ETT along the ETT delivery path and a delivery mechanism configured to deliver the ETT within the trachea.

Further, as another non-limiting example, an ETT delivery system is disclosed which may include swing arm configured to rotate about an axis and a rail system for guiding insertion of an ETT. The rail system further may include a guide rail with one or more rails configured to at least partially define the motion of the swing arm. Further, a laryngoscope blade may be coupled to the guide rail and a drive-down mechanism may be configured to effect motion of the swing arm.

As another non-limiting example embodiment, an ETT delivery system is disclosed including a rail system for delivering an ETT into the trachea. The system further includes a blade coupled to the rail system and a positioner operatively linked with the rail system to enable movement in one or more degrees of freedom in positioning the ETT. Further, the ETT delivery system includes a delivery mechanism operatively linked with the integrated rail system to deliver the ETT within the trachea. Methods for use of the ETT delivery system are further provided.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

As described in more detail below, an ETT delivery system is provided to improve ETT positioning and intubation of a patient. Specifically, various methods and systems for delivery of an ETT for intubation are provided. In one example embodiment and as described below, an ETT delivery system is disclosed. The ETT delivery system may include a swing arm configured to rotate about an axis and a rail system for guiding insertion of an ETT. The rail system further may include a guide rail with one or more rails configured to at least partially define the motion of the swing arm. Additionally, a video laryngoscope blade may be coupled to the guide rail and a drive-down mechanism may be configured to effect motion of the swing arm.

As another embodiment, an ETT delivery system is provided including a rail system for pre-positioning an ETT within the airway. The system further may include a blade coupled to the rail system and a positioner operatively linked with the rail system to enable movement in one or more degrees of freedom in positioning the ETT. Further, the ETT delivery system may include a delivery mechanism operatively linked with the integrated rail system to deliver the ETT within the trachea. In one example, the rail system may define the ETT delivery path and the delivery system may delivery the ETT along the path. The delivery path may include one or both of position components and distance components. For example, the delivery system may be configured to deliver the ETT along a predetermined travel distance. This predetermined travel distance may depend on the blade, the size of the ETT tube or blade, the size of the patient, etc. For example, and not as a limitation, the predetermined travel distance may be set at 10 centimeters. Such distance is provided as an example and not as a limitation.

Further, although described in regards to intubation, similar delivery systems may be used to provide positioning of tubes or delivery devices for bronchoscopy or other systems.

Further, as another example, a method for positioning an ETT using an ETT delivery system is provided. In one embodiment, the method may include determining a travel distance for an ETT for intubation and correspondingly adjusting a rail system of the ETT delivery system and determining a travel path for an ETT for intubation and correspondingly adjusting a rail system of the ETT delivery system. Further, the method may include engaging an ETT along the rail system and delivering the ETT into the trachea.

Figure 1:
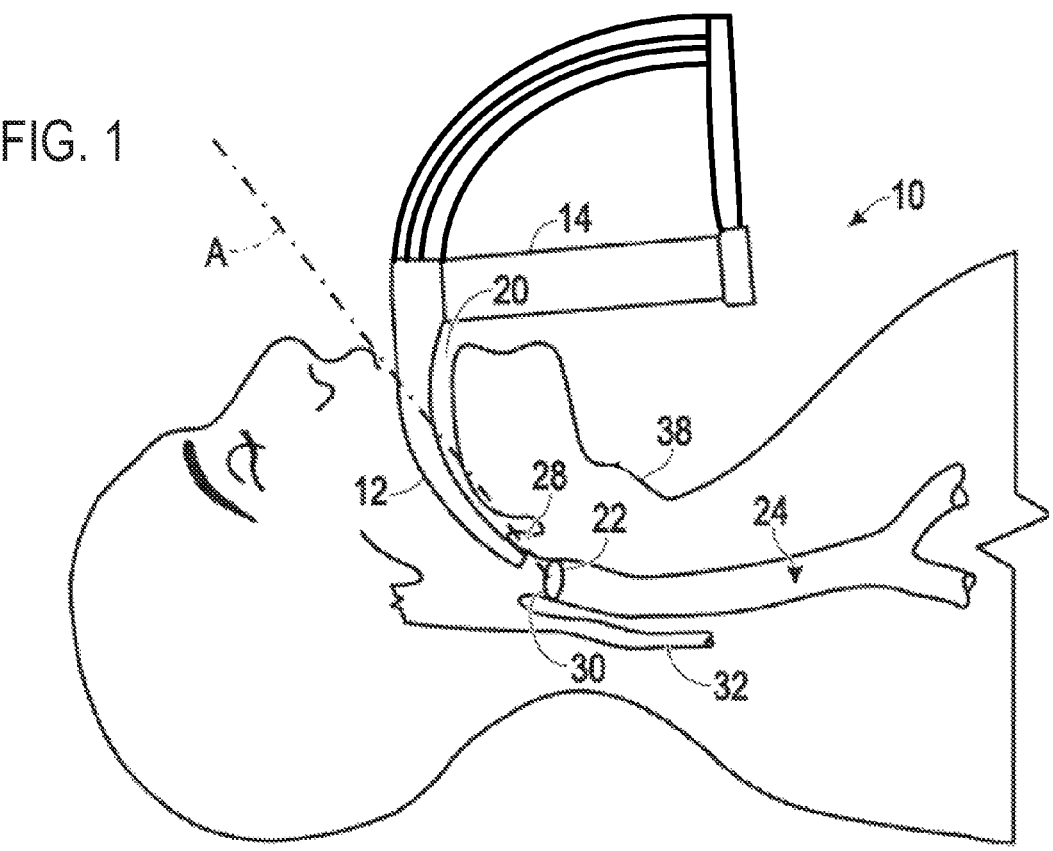
FIG. 1 shows a schematic view of an example intubation device as used to intubate a patient.

Turning first to FIG. 1, a schematic view of an ETT delivery system or intubation device 10 as used to intubate a patient is shown. Intubation device 10, in its most basic form, may include a blade 12 and a handle unit 14. As described in more detail below, in some embodiments, the handle unit and blade may be an integrated unit. In other embodiments, the handle unit and blade may be separate units adapted to be releasably coupled together for use. In such examples, the blade may be detached from the handle unit. For example, in one embodiment, the blade may be detached from the handle unit during use such that the ETT and blade remain coupled during the intubation. The ETT and blade can then be disposed as a single unit. Alternatively, the blade may be separable from the handle unit to enable sterilization of one or both of the blade and handle unit.

As shown, blade 12 may be adapted to be inserted into a patient's trachea 24 via an upper airway of a patient, i.e., via a patient's mouth 20 and vocal cords 22. FIG. 1 also illustrates one of many possible paths during the blade placement. As shown in FIG. 1, epiglottis 28 and glottis 30 are in the front of vocal cords 22. Esophagus 32 is under trachea 24. Trachea 24 is located anterior to esophagus 32. Two cavities, trachea 24 and esophagus 32, are adjacent each other.

FIG. 1 shows that blade 12 is inserted into the mouth and a blade tip is positioned in front of the trachea opening along a line A. When it is determined that blade 12 is at the opening of trachea 24, the ETT (not shown) is pushed into trachea 24 through vocal cord 22. Once the ETT is in the trachea, blade 12 is removed from trachea 24 and the intubation is completed. The ETT tube remains in trachea 24 for a period as required for the medical procedure. Further, in some embodiments, the blade 12 may be provisionally left inside of the oral cavity along with inserted ETT during the procedure. Further in such embodiments, blade 12 may be configured to provide an airway and/or to provide or function as a mouth guard. Such a configuration will be discussed in more detail below in reference to FIG. 15.

Figure 2:
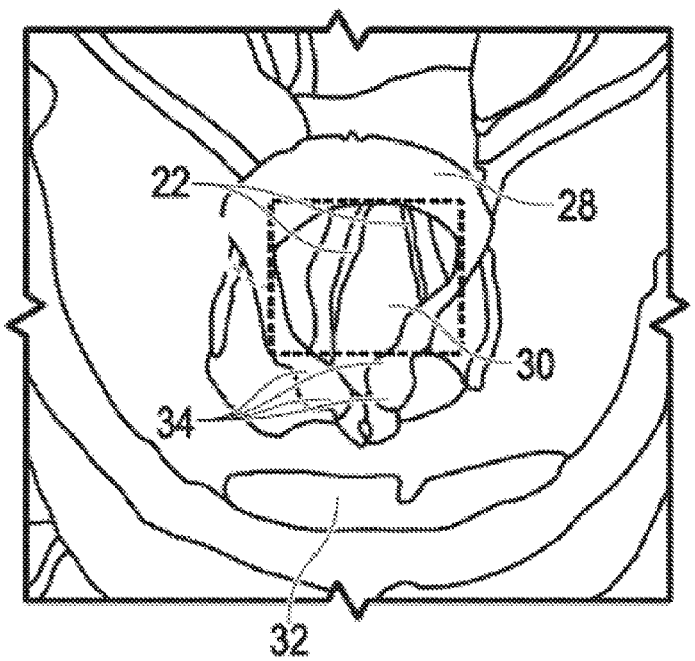
FIG. 2 shows a view of a trachea opening, an esophagus opening, and their surroundings.

As reference for use of the described ETT delivery system, FIG. 2 shows a view of a trachea opening, an esophagus opening and their surroundings. The trachea is an open tube-like cartilage structure with vocal cords 22 at its opening while esophagus 32 is a muscle and connective tissue structure collapsed in the absence of swallowing. The shape of the trachea opening or the vocal cords is substantially different from the shape of the esophagus opening in the size, and the anatomical relationship to epiglottis 28, glottis 30 and arytenoids cartilages 34. As described in more detail in U.S. patent application Ser. No. 11/893,536 filed Aug. 15, 2007 for SYSTEMS AND METHODS FOR INTUBATION and U.S. patent application Ser. No. 12/764,804, filed Apr. 21, 2012 entitled INTUBATION SYSTEMS AND METHODS BASED ON AIRWAY PATTERN IDENTIFICATION, both disclosures herein incorporated by reference for all purposes, various methods and systems may be used to assist in determining accurate delivery and positioning of the ETT in the tracheal and distinguishing the trachea opening from the esophagus opening.

With current devices, positioning of the ETT in the trachea opening may be difficult due to issues which arise in properly positioning the ETT in situations where view of the vocal cords may be difficult. As lack of breathing may result in brain death within 2 minutes, it is important to establish a protected airway by performing the intubation procedure quickly, accurately and non-traumatically when in need. Traditional intubation methods, such as direct laryngoscopy, depend on direct eye view of the airway opening and vocal cords. Further, the traditional intubation methods rely on left and right hand coordination (left hand holding laryngoscope and right hand inserting the ETT). In some cases, estimated at more than 20% of the cases, view of the vocal cord may be difficult. Further, where viewing is obscured, the left and right hand coordination may be distressed presenting further difficulties in ETT insertion. The lack of visual sighting may result in a "cannot see, cannot intubate" scenario.

Likewise, with current video laryngoscopy, such as indirect laryngoscopy, ETT positioning depends on indirect (camera) view of the airway opening and vocal cords. The left and right hand coordination for ETT insertion may be even more difficult with indirect laryngoscopy due to the indirect viewing. For example, the left hand controlled camera view (1D), eye vision (3D) of the screen (1D) and right hand ETT insertion (3D) under camera view (1D) may result in difficulties with correct positioning. Such difficulties may be referred to "can see (by camera) but cannot intubate" scenario.

As described in more detail below, an ETT delivery system is provided to address difficulties which arise in the "cannot see cannot intubate" and "can see (by camera) but cannot intubate" scenarios. Specifically, an ETT delivery system including a rail guide system is provided. Further, in some embodiments, the ETT can be driven down mechanically or manually along the intended path on a camera view. It should be appreciated that mechanical intubation movement may be conducted by an operator directly, such as through a joystick or other manual control. Alternatively, in some embodiments, the intubation movement may be driven electronically. Further, the intubation movement may be controlled and driven remotely through some other form of digital recognition or artificial intelligence, such as, but not limited to pattern recognition and pattern matching.

Figure 3:
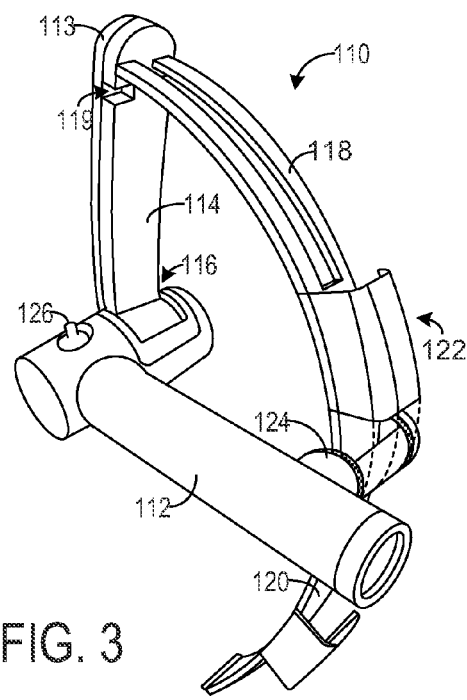
FIG. 3 shows a non-limiting example of an intubation device in accordance with an embodiment of the present disclosure as used to intubate a patient.

Turning now to FIG. 3, a partially exploded view of a non-limiting example of an ETT delivery system or intubation device 110 is shown in accordance with an embodiment of the present disclosure. In the illustrated example, intubation device 110 includes a handle unit 112 coupled to support 113 and further coupled to a delivery mechanism, such as swing arm 114. While illustrated as substantially L-shaped, it will be understood that handle unit 112 and support 113 may comprise any suitable shape without departing from the scope of the present disclosure. Swing arm 114 may be disposed to move along axis 116. In other embodiments, a delivery mechanism instead of, or in addition to, swing arm 114 may be utilized.

It should be appreciated that swing arm 114 may be configured to rotate about axis 116 via any suitable mechanism or combination of mechanisms. For example, in some embodiments, arm 114 may be coupled to an electro-mechanical device (e.g., a motor) to effect motion of arm 114. Arm 114 may be coupled to such electro-mechanical devices directly or via one or more mechanisms (e.g., belt drive, worm gear, lead screw). In other embodiments, arm 114 may be user-actuatable (e.g., by applying pressure to the free end of swing arm 114). In such embodiments where arm 114 is user-actuatable, intubation device 110 may further comprise one or more resistance mechanisms (e.g., springs, pneumatic cylinder, pressure sensors, etc.) configured to resist rotation of swing arm 114 about axis 116.

Intubation device 110 further comprises a rail system or track system including guide rail 118. The rail system provides a guide for ETT insertion. Guidance may include one or more of positioning the ETT, positioning the ETT a predetermined travel distance, guiding the ETT along an ETT delivery path, assisting with fine positioning of the ETT, etc. In some examples, a blade may be integrated into the rail system and/or attached to the rail system.

As an example, and not as a limitation, guide rail 118 may be configured in some embodiments to at least partially guide the motion of swing arm 114 via one or more guide structures 119 of swing arm 114. Guide structures or features 119 may be configured to limit undesirable (e.g., lateral) motion of swing arm 114. Use of the guide rail enables a delivery mechanism to accurately deliver the ETT in position along the guide rail. Although described in regards to use of a guide rail as part of the rail system, in some embodiments, the rail system may not include a guide rail 118. For example, an example intubation device comprising an alternate guide mechanism is discussed in greater detail below in reference to FIGS. 6-8.

While illustrated as notches configured to slide along guide rail 118, it will be understood that guide structures 119 may comprise any mechanism or combination of mechanisms configured to interact with rail 118. For example, guide rail may include one or more guide structures for releaseably engaging and/or guiding ETT insertion. In other embodiments, guide structures 119 may comprise one or more rollers (e.g., wheels, bearings, etc.) configured to interact with guide rail 118. In such embodiments, the rollers may be configured to follow a groove and/or other features of guide rail 118. Such rollers may be considered as part of the delivery mechanism of the system.

Although intubation device 110 is illustrated in a partially exploded view, rail 118 may be directly coupled to support 113 and laryngoscope blade 120 (e.g., via pivot, snap-in, and/or adhesive). Said coupling may be configured to allow for separation of guide rail 118 and/or blade 120 from the remaining elements of intubation device 110. Separation may facilitate sterilization, reuse, and/or disposal. While illustrated as two rails oriented side-by-side along a common radius of axis 116, it will be understood that guide rail 118 may comprise any number of individual rails in any orientation.

Blade 120 may be a video laryngoscope blade. In some examples, blade 120 may comprise one or more sensors at the leading edge. Sensors may comprise imaging sensors and/or tracheal specific sensors. Data from the sensors may be utilized to provide feedback to a user (e.g., via a display device). In other embodiments, data from the sensors may be utilized by one or more guidance systems configured to at least partially control the motion of an ETT during use of intubation device 110. In some examples, the blade may include an ETT steering mechanism as described in more detail below.

Intubation device 110 further may comprise an arm stop 122. In some example embodiments, arm stop 122 may be configured to temporarily couple an ETT to guide rail 118 and/or blade 120 and/or to guide motion of the ETT during use of intubation device 110. Accordingly, arm stop 122 may comprise one or more coupling guides (e.g., tab, pressure fitting, and/or adhesive) configured to temporarily couple the ETT to guide rail 118 and/or blade 120 for insertion into a patient's trachea during use of intubation device 110. Moreover, in some embodiments, arm stop 122 may be further configured to limit rotation of swing arm 114 about axis 116 (e.g., by directly contacting swing arm 114).

Though arm stop 122 is illustrated as being coupled to guide rail 118, it will be understood that arm stop 122 may comprise any suitable orientation. In some embodiments, as illustrated by the dashed outline, arm stop 122 may be coupled to positioner 124. In other embodiments, arm stop 122 may be coupled to blade 120 and/or to one or more positions along the rail system.

As illustrated, guide rail 118 is configured to define, in whole or in part, motion of swing arm 114 in a substantially radial path about axis 116. However, it will be understood that the path of swing arm 114 may comprise any suitable shape. Accordingly, guide rail 118 may be further coupled to handle unit 112 through positioner or adjustment point 124. As such, the motion of guide rail 118 and blade 120 may be adjustable at least in part by positioner 124. Positioner 124 may comprise one or more adjusters (e.g., grooves, followers, and/or pressure fittings) configured to adjust orientation of guide rail 118 and/or blade 120. For example, positioner 124 may be configured to adjust, among other characteristics, the travel distance, curvature, and/or orientation of an ETT coupled to swing arm 114 and/or blade 120.

In some embodiments, positioner 124 may be adjustable via one or more user-actuatable mechanisms (e.g., switch, knob, button, and/or slider). In other embodiments, such adjustment may be performed by one or more electromechanical devices (e.g., a motor). In such embodiments, adjustment may be performed, in whole or in part, via a guidance system. Such a guidance system may be configured to utilize data from one or more sensors coupled to an edge of blade 120.

Intubation device 110 further comprises input device 126 coupled to handle unit 112. While illustrated as a joystick oriented along the far edge of handle unit 112, it will be understood that input device 126 may comprise any one or more input mechanisms (e.g., button, knob, slider, directional pad, and/or touch-sensitive device) oriented in any suitable position on and/or within handle unit 112. In some embodiments, the handle unit may further include an interface display to assist with ETT insertion and positioning. For example, the handle unit may include a screen or monitor providing feedback from a sensor device or capture device on the stylet tip. It should be appreciated that in some embodiments, the input device and/or any interface display may be remote from the intubation system.

In one example, such as a sensory stylet, a joystick may be provided for thumb operation, such as for directional control. Further, an index finger motion control may be used for video laryngoscope blade and style. Such controls oriented for use by the thumb and index finger improve the ergonomics of the ETT delivery system enable ease of operation.

Figure 12:
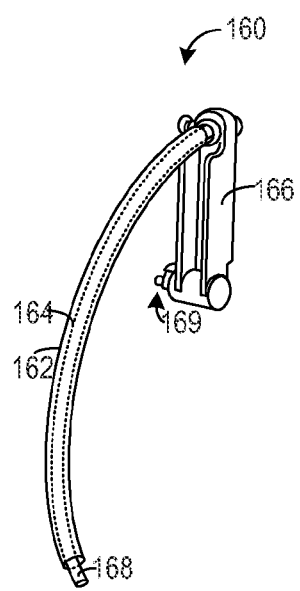
FIG. 12 shows an embodiment of an example stylet assembly for use with an intubation device and an ETT in accordance with embodiments of the present disclosure.

Input device 126 may be configured to provide user control over motion of swing arm 114 and/or over adjustment of positioner 124 and/or an intubation stylet (e.g., stylet tip 168 of FIG. 12). In some embodiments, input device 126 may comprise one or more mechanisms configured to translate user input into one or more electrical signals. In other embodiments, input device may be coupled to one or more mechanisms (e.g., guide wires, pulleys, and/or gears) configured to translate user input into mechanical motion. It will be understood that these scenarios are presented for the purpose of example, and are not intended to be limiting in any manner.

In some embodiments, input device 126 may be configured to provide user control over one or more sensors (e.g., imaging sensors and/or chemical sensors) coupled to blade 120, an ETT, and/or a stylet. In other embodiments, input device 126 may be configured to provide control over a stylet coupled to, or oriented within, the ETT. A further example stylet is discussed in greater detail below in reference to FIGS. 8 and 9.

In some embodiments, guide rail 118, blade 120, positioner 124 and arm stop 122 may form a substantially integrated or unitary unit. In other embodiments, one or more of guide rail 118, blade 120, positioner 124 and arm stop 122 may be removably detached for cleaning, sterilization or replacement.

Figure 4:
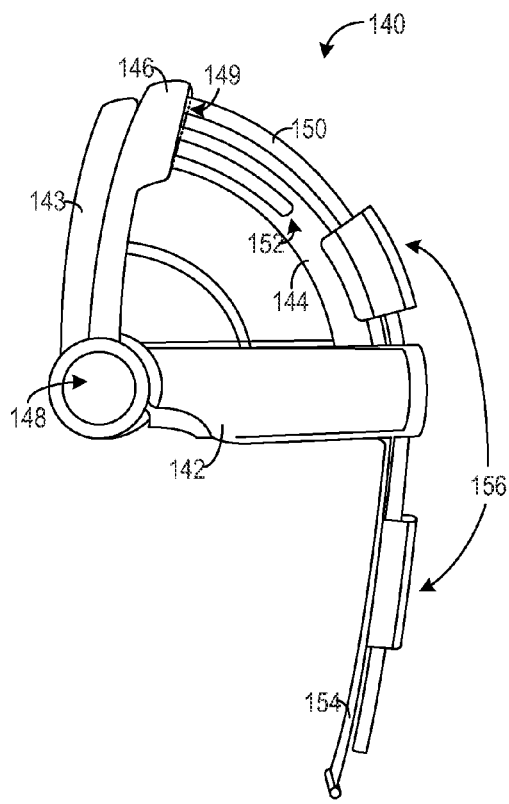
FIG. 4 shows a non-limiting example of an intubation device in accordance with another embodiment of the present disclosure as used to intubate a patient.

FIG. 4 shows a non-limiting example of an intubation device 140 in accordance with another embodiment of the present disclosure as used to intubate a patient. As with FIG. 3, intubation device 140 comprises a handle unit 142 coupled to a support 143 and further coupled to a guide rail 144. While illustrated as substantially L-shaped, it will be understood that handle unit 142 and support 143 may comprise any suitable shape without departing from the scope of the present disclosure. It should be appreciated that the device 140 may be operatively coupled to the ETT, blade and/or stylet to function mechanically and/or electronically with one or more of the ETT, blade and/or stylet.

In the illustrated embodiment, and as described in more detail below, handle unit 142 and guide rail 144 form a delivery unit separable from the blade. The blade may be detached from the delivery unit such that the delivery unit may be reused. Further, the delivery unit may be sterilized and cleaned separate from the blade and any sensors. Moreover, in some embodiments, the blade and/or the delivery unit may be separately disposed such that one or both of the blade and/or the delivery unit may be reused or replaced.

Turning back to FIG. 4, intubation device 140 further includes swing arm 146 coupled to handle unit 142 at axis 148. Swing arm 146 may be configured to rotate about axis 148 via any suitable mechanism or combination of mechanisms. In other embodiments, intubation device 140 may comprise a different and/or additional delivery mechanism than swing arm 146. In some embodiments, arm 146 may be coupled to an electro-mechanical device (e.g., a motor or servo) to effect motion of arm 146. Arm 146 may be coupled to such an electro-mechanical device directly or via one or more mechanisms (e.g., belt drive, worm gear, lead screw). In other embodiments, arm 146 may be user-actuatable (e.g., by applying pressure to the free end of swing arm 146). In such embodiments where arm 146 is user-actuatable, intubation device 140 may further comprise one or more resistance mechanisms, such as, but not limited to, springs, pneumatic cylinders, sensors, or other biasing mechanisms. Such resistance mechanisms may be adapted to resist rotation of swing arm 146 about axis 148.

As illustrated, swing arm 146 comprises a cavity 149 configured to temporarily couple ETT 150 and/or a stylet (e.g., all or part of stylet assembly 160 of FIG. 12) to swing arm 146. It will be understood that swing arm 146 may comprise any one or more engagement structures (e.g., edge, cavity, slot, pin, interlock and/or tab) configured to provide interaction with ETT 150 such that the rotation of swing arm 146 may effect motion of ETT 150 along a path defined by all or part of guide rail 144. It will be further understood that swing arm 146 may comprise one or more mechanisms configured to provide electronic and mechanical interaction with blade 154, ETT 150, a stylet, and/or sensors thereof.

As illustrated, guide rail 144 may comprise a plurality of rails oriented radially from axis 48. However, it will be understood that guide rail 144 may comprise any number of individual rails in any orientation. Further, although shown as an extended guide rail, guide rails 144 may be any suitable structure to provide engagement and positioning of the ETT. As non-liming examples, guide rails 144 may be a single guide rail, a recessed track, a raised guide, a tab positioner, etc.

Guide rail 144 may further comprise one or more guide structures configured to restrict motion of swing arm 146 and to accommodate varying sizes and lengths of ETT 150 and/or a stylet. For example, the rails of guide rail 144 may form a groove terminating at stop 152 such that swing arm 146 may not rotate substantially past stop 152. In other embodiments, the motion of swing arm 146 may be limited via interaction (e.g., collision) with one or more features of blade 154.

Blade 154 may comprise one or more tube guides 156 configured to temporarily couple ETT 150 to blade 154. Guides 156 may be configured to guide motion of ETT 150 during use of intubation device 140. Accordingly, tube guides 156 may comprise one or more coupling guides (e.g., tab, pressure fitting, and/or adhesive) configured to temporarily couple the ETT to blade 154 for insertion into a patient's upper airway during use of intubation device 110. Tube guides 156 may be further configured to limit (e.g., via collision) motion of swing arm 146 instead of, or in addition to, stop 152.

As illustrated, in some embodiments, blade 154 may be detachable from the intubation device 140. In such embodiments, both the blade and the delivery system may be separately cleaned, sterilized, or otherwise re-used, thus possibly decreasing cost and waste product. As another example, in a disposable use case scenario, detachability may allow for easy swapping of disposable instances of blade 154.

Figure 5:
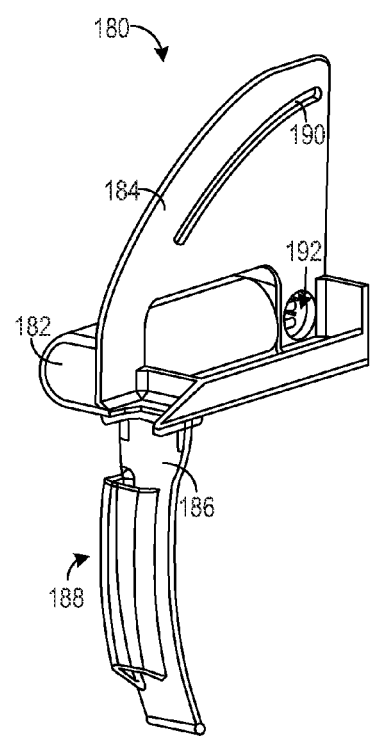
FIG. 5 shows a non-limiting example of an integrated rail and blade assembly in accordance with another embodiment of the present disclosure.

FIG. 5 shows a non-limiting example of another ETT delivery system, specifically a rail and blade assembly 180 in accordance with another embodiment of the present disclosure. Assembly 180 may be utilized in combination with one or more elements (e.g., swing arm 114 of FIG. 3) to realize an intubation device. In other embodiments, assembly 180 may be configured to be utilized in a stand-alone use case scenario.

Assembly 180 comprises handle unit 182 coupled to guide assembly 184 and blade 186. Blade 186 may include one or more positional guides (e.g., tube guide 188) configured to guide motion of an ETT during use of assembly 180. While illustrated as a substantially hollow tube into which an ETT is inserted, it will be understood that tube guide 188 may comprise one or more positioners (e.g., pressure fitting, tab, groove, and/or adhesive) configured to guide the motion of an ETT during use of assembly 180. Guide assembly 184 may comprise one or more grooves 190. While illustrated as a single groove in a substantially radial path, it will be understood that grooves 190 may comprise any number of individual grooves of any size and/or shape or other groove features.

Assembly 180 may further comprise motor assembly 192. Motor assembly 192 may comprise one or more electromechanical devices (e.g., motor) and may further comprise one or more mechanisms (e.g., worm drive, lead screw, and/or gears) configured to translate the motion of the electromechanical device. Motor assembly 192 may be configured to effect motion of guide assembly 184. In such embodiments, an ETT may be temporarily coupled to guide assembly 184 via an adjustable attachment point along groove 190.

In other embodiments, motor assembly 192 may be configured to effect motion of a swing arm or other delivery mechanism, the motion of said swing arm being at least partially defined by grooves 190.

Figure 6:
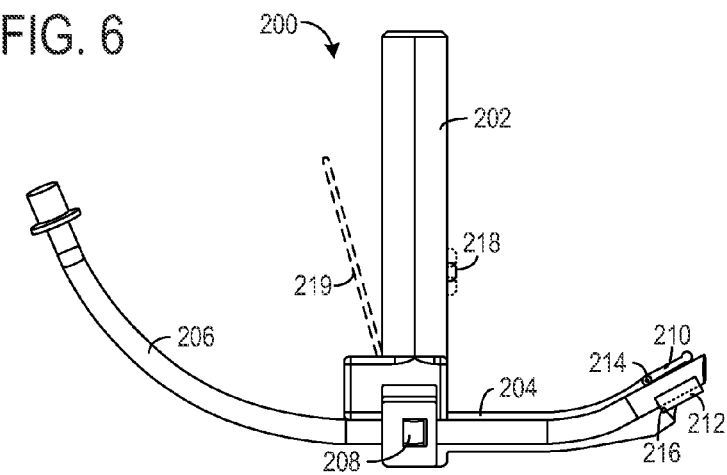
FIG. 6 shows a non-limiting example of an intubation device in accordance with an embodiment of the present disclosure as used to intubate a patient.

As mentioned above, in some embodiments, guide mechanisms other than a guide rail (e.g., guide rail 118 of FIG. 3 and/or guide rail 144 of FIG. 4). For example, FIG. 6 shows a non-limiting example of an intubation device 200 in accordance with an embodiment of the present disclosure as used to intubate a patient. Intubation device comprises a handle unit 202 coupled to guide mechanism 204. Guide mechanism 204 may comprise one or more features (e.g., track, groove, tabs, etc.) configured to interact with ETT 206 in order to at least partially define the motion such as the positioning of ETT 206. In some examples, such features may be configured to guide ETT. For example, the features may contact or enclose ETT 206 in whole or in part. Thus, guide mechanism 204 (also referred to in this embodiment as a rail system for defining the ETT delivery path) may include a pass-through guidance system. The pass-through system operates as the rail and assisting in the guidance and positioning of the ETT. As such, intubation device 200 may be configured such that ETT 206 may be inserted into handle unit 202 and/or guide mechanism 204. In some embodiments, guide mechanism 204 may be detachable from the remaining elements of intubation device 200 to allow for easy sterilization or disposal of guide mechanism 204 and/or mechanisms and sensors coupled thereto. One example of an intubation device comprising a detachable guide mechanism will be discussed in greater detail below in reference to FIGS. 9A-B.

Intubation device 200 further comprises one or more rollers 208 configured to effect motion of ETT 206 along guide mechanism 204. Although illustrated as a single roller on the side of ETT 206, it will be understood that rollers 208 may comprise any number of rollers in any orientation. It will be further understood that rollers 208 may comprise any suitable mechanism or combination of mechanisms (e.g., wheels, drums, belts, etc.) configured to effect motion of ETT 206.

In some embodiments, control and direction of motion of ETT 206 through intubation device 200 may include operation of a tip control mechanism. In some embodiments, the tip control mechanism may be included as part of the blade, such that the blade has an ETT steering mechanism to adjust the ETT tip direction. Although shown in regards to FIGS. 6-8, it should be appreciated that any one of the disclosed embodiments may include a tip control mechanism to further assist in positioning the ETT.

In one example, the tip control mechanism or ETT steering mechanism comprises an active and passive lip configuration. Also, referred to herein as a master and slave lip configuration. For example, a passive lip, such as upper lip 210 and an active lip, bottom lip 212 may engage the ETT tube along an ETT delivery path. It should be appreciated that in other embodiments, the lips may move independently to increase exposure and view of the vocal cord. Further split lips or varied numbers of lips may be used.

As discussed below in regards to the illustrated example, the lips may be maintained in a closed position until the ETT is pushed through. The ETT pushes the lips into an open position. In the closed position, initial blade insertion into the mouth and through to the trachea easier. FIG. 7B shows a closed position for blade insertion in dashed lines. The closed position may protect the ETT and any camera or sensor that may be included with the ETT. For example, the closed position may protect the ETT from patient artifacts, such as patient saliva or sputum, food residues and blood. It is noted that in some examples, the closed position illustrated in FIG. 7B may further enable effective operation of sensors attached to the underside of the bottom lip (e.g., sensors 226 of FIG. 8). Further, in some embodiments, the lower lip may close up while the upper lip stays in position. The lower lip may thus rotate up to meet the upper lip in the closed position. With release of the ETT, the lower lip is pushed downward (away from the upper lip) In such examples, the camera view (positioned in some examples below the lower lip) may be facilitated when the lower lip is in a closed position and may engage an active lever when in an open position.

Once pushed through the lips, the active lip may control the tip up movement of the ETT into position due to the anatomical position of the vocal cords and trachea opening. Thus, in this way, the lip control mechanism, such as the active and passive lip, may control the direction of the ETT along its third degree movement. For example, the lip control mechanism may control the forward and backward movement of the ETT. In some examples, the blade may be detached for sterilization. The tip control mechanism may further provide a coupling for a camera.

It should be appreciated that the ETT delivery system described herein defines the ETT delivery path. In defining the ETT delivery path, it may be possible to control the ETT tip upward such as through the lip control mechanism (additional fine positioning may be provided through a sensor and/or stylet system). It is noted that in prior systems since the vocal cord is up and slightly left, positioning depends on midline or slightly left blade insertion and routine external cricoids pressure application (standard current practice) to move tracheal externally to the middle of the neck to facilitate ETT insertion. With the present invention and control of the ETT tip angle by the lip control mechanism, plus rotation movement provide by features such as 166 at the ETT end junction, it is possible to adequately and effectively move the ETT tip to the left into the desired position. Although a stylet may further enhance positioning capabilities, such as providing additional definition of the ETT delivery path, such a stylet may not be necessary with all systems.

In the illustrated example, upper lip 210 may be coupled to guide mechanism 204 at axis 214 such that upper lip 210 may be configured to pivot about axis 214. In the illustrated example, upper lip 210 comprises a resistance mechanism or biasing mechanism (e.g., spring, pneumatic cylinder, counterweight, etc.) configured to resist pivoting about axis 214 such that upper lip 210 may maintain contact with ETT 206. Although shown with upper lip having the resistance mechanism, it should be appreciated that bottom lip may further include or alternatively include such resistance mechanism. Moreover, in some embodiments, no resistance mechanism may be included.

Furthermore, upper lip 210 may comprise a laryngoscope blade (e.g., blade 120 of FIG. 1) and/or one or more sensors (e.g., imaging, tracheal-specific, etc.).

Similar to upper lip 210, bottom lip 212 may be coupled to guide mechanism 204 at axis 216 such that upper lip 210 may be configured to pivot about axis 216. Accordingly, the pressure applied by upper lip 210 may allow ETT 206 to travel in a direction substantially defined via bottom lip 212 (in alternate embodiments the travel path may be defined by the upper lip or the combination of the upper and lower lip). As such, in the illustrated embodiment, bottom lip 212 may be configured to perform one or more functions similar to positioner 124 of FIG. 3.

Intubation device 200 may further comprise lip adjuster 218 coupled to handle unit 202 and configured to adjust orientation of bottom lip 212. As illustrated, lip adjuster 218 may comprise a user-actuatable input device configured to slide (illustrated as dashed outline) along handle unit 202. For example, the lip adjuster may be a sliding down knob. The lip adjuster may be configured to mechanically position the ETT and also control the third degree movement electronically.

As another example, in some embodiments, intubation device 200 may comprise lip adjuster lever 219 configured to adjust bottom lip 212 instead of, or in addition to, lip adjuster 218. In such embodiments, lip adjuster lever 219 may be configured to be actuated via a squeezing motion of a user's hand while holding handle unit 202.

Thus, lip adjuster 218 may comprise any suitable mechanism (e.g., button, knob, joystick, etc.) electrically and/or mechanically coupled to bottom lip 212 in order to provide adjustment of the active lip (such as bottom lip 212) or lips. In some embodiments, lip adjuster 218 and/or lip adjuster lever 219 may be configured to, and/or coupled to an input device configured to, effect motion of rollers 208 in order to effect motion of ETT 206.

Figure 7A:
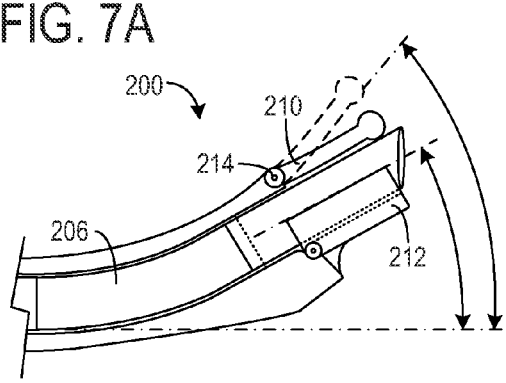
FIG. 7A shows a close-up view of a portion of the intubation device of FIG. 6.
Figure 7B:
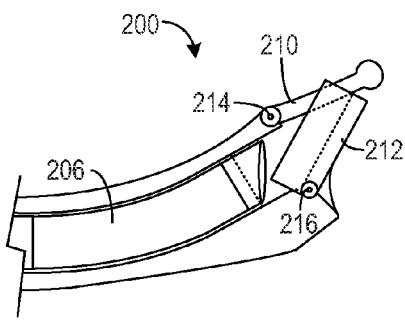
FIG. 7B shows a close-up view of a portion of the intubation device of FIG. 6 with the lips in a closed position.

FIG. 7A shows a close-up view of a portion of intubation device 200 of FIG. 6. As illustrated by the dashed outline, upper lip 210 may be configured to pivot about axis 214. The position of upper lip 210 is determined via the orientation of bottom lip 212 and/or the size, shape, and/or existence of ETT 206.

In some embodiments, as illustrated, bottom lip 212 may be configured to form a guide (e.g., channel, groove, etc.) configured to at least partially enclose ETT 206. Although illustrated as a continuous feature along the length of bottom lip 212, it will be understood that said guide may comprise any suitable configuration. Thus, as described above, tip control mechanism may define a delivery path for the ETT, enabling both distance positioning and angle positioning.

FIG. 7B shows a close-up view of a portion of the intubation device 200 of FIG. 6 with lips 210 and 212 in a closed position. In the closed position (e.g., no ETT inserted or, as illustrated, ETT 206 has not reached lips 210 and 212), upper lip 210 may be in contact with all or part of bottom lip 212. Accordingly, lips 210 and 212 may be configured to protect ETT 206 during insertion of device 200. As illustrated, in some examples, upper lip 210 may not pivot about axis 214 substantially past its "open" position of FIG. 7A (illustrated as a solid outline). Accordingly, the "closed" position of lips 210 and 212 in FIG. 7B may be realized via pivoting of bottom lip 212 about axis 216 towards upper lip 210. In other embodiments, upper lip 210 and/or bottom lip 212 may comprise different resting positions.

Figure 8:
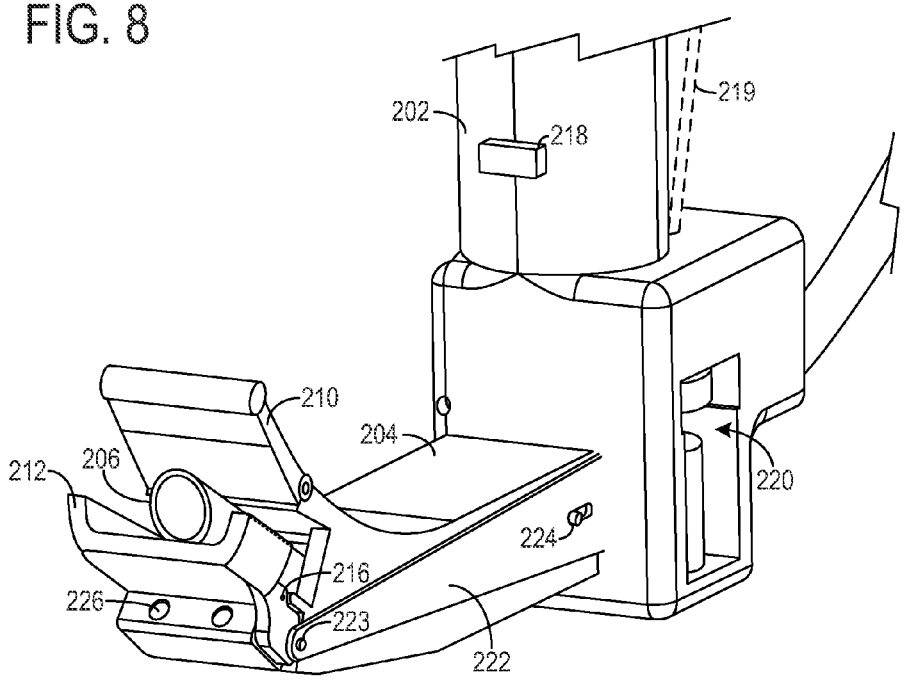
FIG. 8 shows another portion of the intubation device of FIG. 6.

FIG. 8 shows another portion of intubation device 200 of FIG. 6. As illustrated, handle unit 202 further comprises one or more rollers 220. Rollers 220 may be substantially similar to rollers 208 such that rollers 220 may be configured to effect motion of ETT 206 along guide mechanism 204.

As previously described, lip adjuster 218 and/or lip adjuster lever 219 may be coupled to bottom lip 212 in order to adjust the orientation of bottom lip 212. As illustrated, intubation device 200 comprises a mechanism 222 coupled to bottom lip 212 via pivot 223. Mechanism 222 may be coupled to lip adjuster 218 and/or lip adjuster lever 219. Mechanism 222 may be further configured to slide in a substantially linear motion along pivot 224. Accordingly, mechanism 222 may comprise one or more features (e.g., groove, follower) configured to guide motion of mechanism 222 along pivot 224. In other embodiments, lip adjuster 218 and/or lip adjuster lever 219 may be coupled to one or more mechanisms comprising pivot 224. In such embodiments, motion of lip adjuster 218 and/or lip adjuster lever 219 may be translated into motion of pivot 224. Accordingly, mechanism 222 may be configured to adjust orientation of bottom lip 212 via pivot 223 in response to motion of pivot 224. As mentioned above, bottom lip 212 may be adjustable via any suitable mechanism or combination of mechanisms without departing from the scope of the present disclosure.

Intubation device 200 may further comprise one or more cameras or sensors (indicated schematically at 226) operatively coupled to guide mechanism 204. Sensors may comprise any sensor or combination of sensors as described throughout the application. Although illustrated as two individual sensors located at the edges of the leading edge of guide mechanism 204, it will be understood that sensors 226 may comprise any configuration and/or location For example, in some embodiments, sensors may be located in the middle of the leading edge of guide mechanism 204. In other embodiments, sensors 226 may be coupled to one or more of ETT 206, upper lip 210, bottom lip 212, and any other elements of intubation device 200. For example, in some embodiments, a camera may be position on the side of the lip control mechanism.

As described above, bottom lip 212 may be configured to rotate about axis 216 to adjust the angle of delivery of ETT 206. Furthermore, bottom lip 212 may be adjustable in additional DOF. For example, all or part of bottom lip 212 may be configured to rotate about the major axis of ETT 206. Such rotation may allow for pitch/yaw adjustment of the motion of ETT 206. As another example, all or part of bottom lip 212 may be configured pivot side-to-side. As yet another example, all or part of bottom lip 212 may be configured to extend and/or retract. It will be understood that bottom lip 212 may be configured to be adjustable in multiple DOF. Furthermore, although bottom lip 212 is illustrated as comprising a substantially U-shaped channel, it will be understood that bottom lip 212 may comprise any configuration without departing from the scope of the present disclosure.

Regardless of the configuration of bottom lip 212 and upper lip 210, greater control over the path of ETT 206 may be desired (such as for fine positioning in difficult intubation situations). Accordingly, intubation device may be configured to utilize a stylet, such as stylet body 164, which will be discussed in greater detail below in reference to FIGS. 11 and 12. In such embodiments, a stylet may be configured to provide side-to-side and/or pitch/yaw adjustment of ETT 206. In other embodiments, such a stylet may be configured to provide additional and/or different adjustment of ETT 206.

Figure 9A:
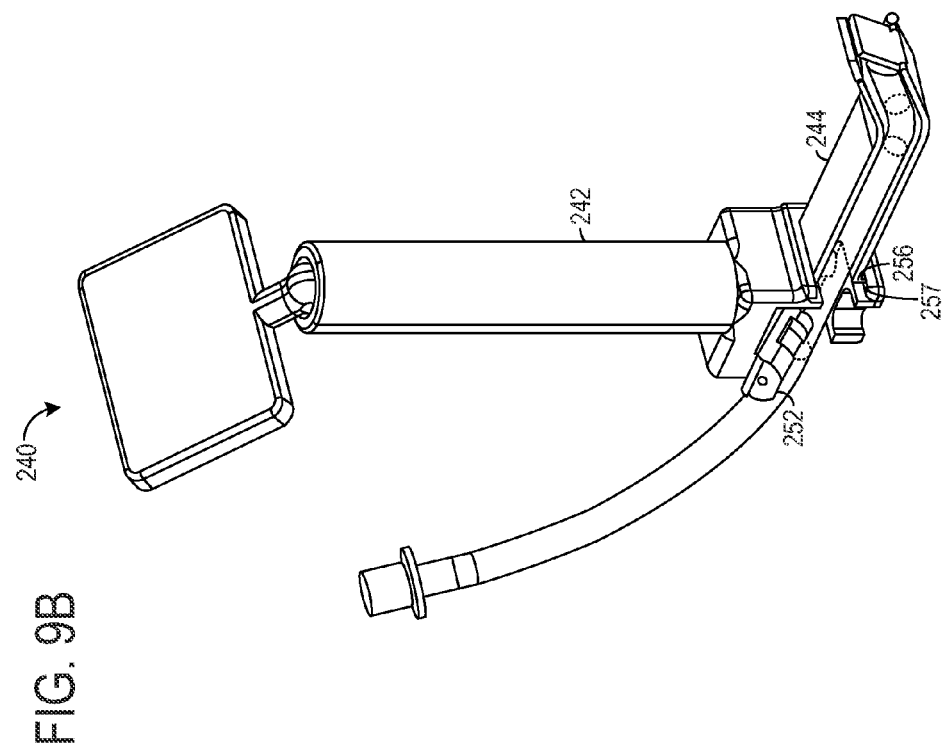
FIG. 9A shows a non-limiting example of a partially exploded intubation device in accordance with another embodiment of the present disclosure.

Turning now to FIG. 9A, a non-limiting example of an intubation device 240 is shown in accordance with another embodiment of the present disclosure as used to intubate a patient. Intubation device comprises a handle unit 242 coupled to guide assembly 244. Similar to guide mechanism 204 of intubation device 200, guide assembly 244 may comprise one or more features (e.g., track, groove, tabs, etc.) configured to interact with ETT 246 in order to at least partially define the motion such as the positioning of ETT 246. In some examples, such features may be configured to guide ETT 246. For example, the features may contact or enclose ETT 246 in whole or in part. Thus, guide mechanism 244 (also referred to in this embodiment as a rail system for defining the ETT delivery path) may include a pass-through guidance system. The pass-through system operates as the rail and assisting in the guidance and positioning of the ETT.

The guide assembly may be considered the blade in some embodiments and may include a video laryngoscope blade. In some embodiments, it is noted that the ETT can be preloaded to the blade. Guide assembly 244 further comprises lips 248 and 249 and sensors 250 to further assist in positioning ETT 246. Lips 248 and 249 may be configured similarly to lips 210 and 212 of FIGS. 6-8, respectively. Sensors 250 may comprise any sensor or combination of sensors as described throughout the application. Although illustrated as a single sensor located at the edges of the leading edge of guide assembly 244, it will be understood that sensors 250 may comprise any configuration and/or location. For example, in some embodiments, sensors may be located in the middle of the leading edge of guide assembly 244.

As illustrated by the partially-exploded view of FIG. 9A, guide assembly 244 may be detachable from handle unit 242. Such detachability may allow for easy insertion of ETT 246 into intubation device 240. Further, in detachable blade scenarios, guide assembly 244 may be detachable from handle unit 242 such that guide assembly 244 may remain in the patient's airway throughout a procedure in order to ensure proper placement of ETT 246. Such scenarios will be discussed in greater detail below with reference to the detachable blade assembly of FIG. 15.

Accordingly, handle unit 242 comprises access assembly 252 to provide easy coupling of ETT 246 and/or guide assembly 244 to handle unit 242. As illustrated, access assembly 252 may be coupled to handle unit 242 at one end such that access assembly 252 may pivot about said end to allow insertion of guide assembly 244 and/or ETT 246. Access assembly 252 may be user-actuatable and/or may be actuatable via one or more other mechanisms (e.g., electro-mechanical actuator). Further, access assembly may be "locked" into a use position (e.g., access assembly 252 pivoted downward from illustrated position such that roller 254 is in contact with ETT 246) via one or more mechanisms (e.g., pressure fitting, snap-in, magnet, spring, groove, etc.).

While discussion is directed towards a pivoting configuration of access assembly 252, it will be understood that access assembly 252 may comprise any suitable configuration without departing from the scope of the present disclosure. For example, in some embodiments, access assembly 252 may be detachable from handle unit 242 via one or more mechanisms (e.g., pressure fitting, magnet, groove, snap-in, etc.) and then re-attachable after insertion of guide assembly 244 and/or ETT 246. As another example, access assembly 252 may be configured to slide to/from the use position in one or more directions.

Figure 9B:
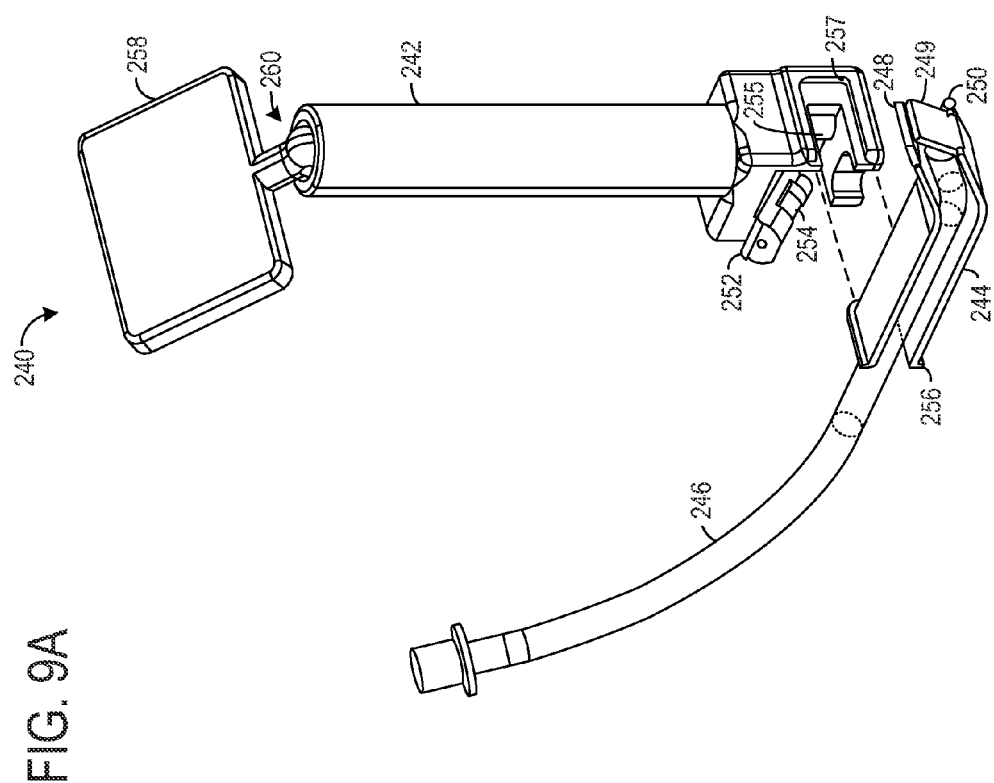
FIG. 9B shows a further view of the example intubation device of FIG. 9A.

Intubation device 200 further comprises one or more rollers 254 and 255 configured to effect motion of ETT 246 along guide assembly 244. In some embodiments, one of rollers 254 and 255 may be configured to spin freely while the other roller effects motion of ETT 246. Although illustrated as two rollers on opposing sides of ETT 246, it will be understood that rollers 208 may comprise any number of rollers in any orientation. It will be further understood that rollers 254 and 255 may comprise any suitable mechanism or combination of mechanisms (e.g., wheels, drums, belts, etc.) configured to effect motion of ETT 246. As shown in FIG. 9A, the locking roller may be raised for blade and ETT assembly. In FIG. 9B, the locking roller may be lower to locate the blade assembly. In some examples the drive rollers may be fully integrated into the blade assembly.

In order to facilitate coupling of guide assembly 244 to handle unit 242, guide assembly 244 and handle unit 242 may comprise flange 256 and groove 257, respectively. Flange 256 may be configured to be at least partially inserted into groove 257. In other embodiments, flange 256 may be coupled to handle unit 242 and groove 257 may be coupled to guide assembly 244. In yet other embodiments, guide assembly 244 may be configured to couple to handle unit 242 via different and/or additional mechanisms (e.g., snap-in fitting, threaded fitting, etc.).

Intubation device 200 further comprises display device 258 coupled to handle unit 242 via ball joint 260. Ball joint 260 may allow for greater flexibility in positioning display device 258 according to individual use-case scenarios. In other embodiments, display device 258 may be coupled to handle 242 via other mechanisms and/or may be detachable from handle unit 242. Once detached in a detachable scenario, display device 258 may remain operable and communicatively coupled to handle unit 242 via a wired and/or wireless connection. Display device 258 may be configured to display information received from sensors 250 to assist with placement of ETT 246 into the patient's airway. In some embodiments, display device 258 may be further configured to receive user input (e.g., via a touch-sensitive surface and/or other coupled user input devices). In such embodiments, display device 258 may be configured to provide control over one or more of lip 248, lip 249, roller 254, and roller 255 via user input. Accordingly, intubation device 200 may comprise one or more mechanisms configured to provide mechanical and/or electrical coupling between handle unit 242 and one or more elements of guide assembly 244 (e.g., lips 248 and 249 and/or sensors 250). In some embodiments, said mechanisms may be integrated with flange 256 and/or groove 257 such that said coupling occurs upon mating of flange 256 and groove 257.

Turning now to FIG. 9B, the assembled intubation device 240 of FIG. 9A. As illustrated, flange 256 of guide assembly 244 has been inserted into groove 257 of handle unit 242. Guide assembly 244 may remain coupled to handle unit 242 via friction between flange 256 and groove 257. In other embodiments, guide assembly 244 may remain coupled to handle unit 242 via any other suitable mechanism or combination of mechanisms. For example, guide assembly 244 may be "locked" via pivoting of access assembly 252 into the use position.

Figure 10:
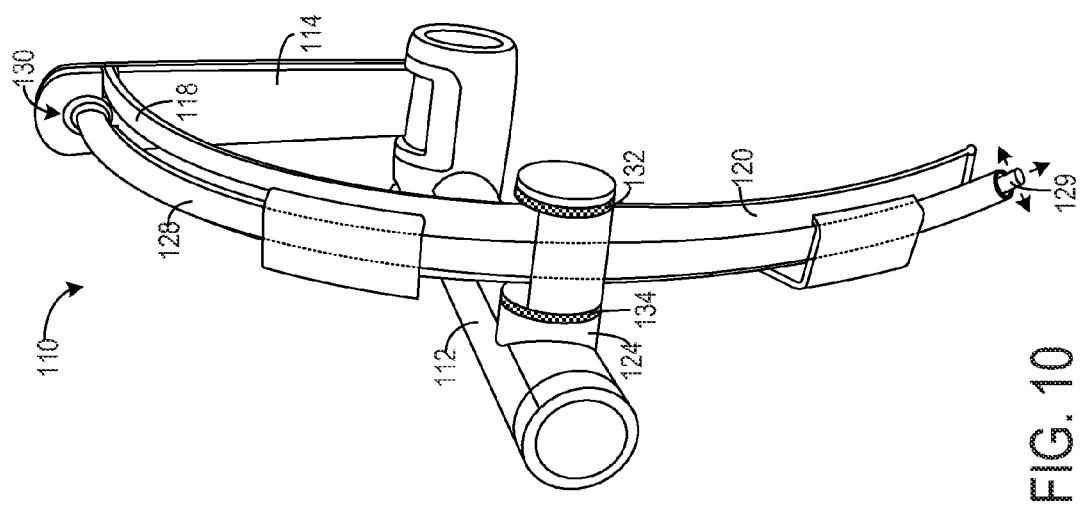
FIG. 10 shows a front-view of the intubation device of FIG. 3 with an ETT.

FIG. 10 shows a front-view of the intubation device 110 of FIG. 3 with an ETT 128 and stylet 129 (e.g., stylet body 164 and stylet tip 168 of FIG. 12). Swing arm 114 may further comprise tube stop 130 configured to temporarily secure one end of ETT 128 such that the rotation of swing arm 114 may effect motion ETT 128 along a path defined by all or part of guide rail 118. Although illustrated as a single, circular feature of swing arm 114 configured to interact with an end of ETT 128, it will be understood that tube stop 130 may comprise any mechanism or combination of mechanisms (e.g., an edge, cavity, and/or tab) configured to interact with all or part of ETT 128 during use of intubation device 110.

As mentioned above in reference to FIG. 3, intubation device 110 may include a positioner, such as positioner 124 configured to provide adjustment of guide rail 118. Such adjustment may at least partially define motion of swing arm 114 and ETT 128 along guide rail 118. In some embodiments, positioner 124 may include user-actuatable input mechanisms or adjusters. Positioner 124 may be configured to modify orientation of guide rail 118 in multiple degrees of freedom (DOFs). For example, positioner 124 may perform "up and down movement" referred to as a first DOF, "right and left movement" referred to as a second DOF, and "forward and back movement" referred to as a third DOF. As another example, positioner 124 may perform adjustment of pitch and/or yaw of guide rail 118. It will be understood that positioner 124 may be configured to provide fewer, additional, and/or different adjustments without departing from the scope of the present disclosure.

It will be understood that intubation device 110 may comprise any number of suitable configurations comprising any number of degrees of freedom, such as 1-3 degrees of freedom. For example, in some embodiments, intubation device 110 may be combined to provide the increased degrees of freedom through a combination of a guide rail with an ETT, a guide rail with an ETT and a stylet, a guide rail with ETT and blade tip articulation, and an ETT and blade tip articulation without a guide rail, among other configurations.

The guide rail may be adjustable via height adjuster 132 and/or depth adjuster 134. Adjusters 132 and 134 may allow for use of intubation device 110 with patients and/or ETTs of varying shapes and sizes. Height adjuster 132 may be configured to move positioner 24 in the y-direction with respect to the point of view of FIG. 10. Such adjustment may be used to configure the travel distance of swing arm 114 and/or the distance between handle unit 112 and the edge of blade 120. Depth adjuster 134 may be configured to move positioner 124 in the z-direction with respect to the point of view of FIG. 10 (e.g., substantially parallel to the length of handle unit 112). Such adjustment may be used to configure the angle of motion of ETT 128. Further, other adjusters may be provided to adjust the angle or position of the ETT and it should be understood that these adjustments are presented for the purpose of example, and that different types and/or number of adjustments may be possible without departing from the scope of the present disclosure.

While illustrated as user-actuatable input mechanisms (e.g., knobs), it will be understood that height adjuster 132 and/or depth adjuster 134 may comprise any mechanism or combination of mechanisms configured to adjust the orientation of positioner 124. For example, in some embodiments, one or both of adjusters 312 and 134 may comprise an electromechanical device (e.g., motor or linear actuator).

In addition to, or instead of, the adjustment provided by positioner 124, the orientation of ETT 128 may be at least partially determined via stylet 129 at least partially oriented within ETT 128. As illustrated, stylet 129 may be configured to be oriented in multiple DOF. Stylets and the orientation thereof will be discussed in greater detail below in reference to FIGS. 11 and 12.

Figure 11:
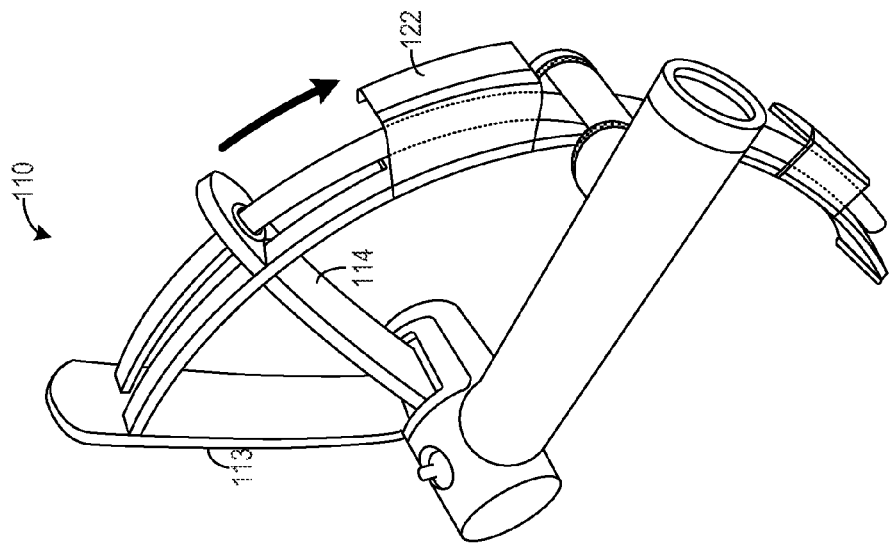
FIG. 11 shows the intubation device of FIG. 3 during use.

FIG. 11 shows the intubation device 110 of FIG. 3 during use. Specifically, swing arm 114 is shown in an intermediate position between a starting position (e.g., position limited by support 113) and an ending position (e.g., position limited by arm stop 122). The drive mechanism for insertion of the ETT may be manually operated and/or computer operated. For example, in some systems, a user may drive the swing arm directly though joystick controls or other user controls based on visual cues or other data. In other embodiments, the swing arm may be remotely controlled based on sensor data or pattern data.

It will be understood that the starting and/or ending position of swing arm 114 may be adjustable. Such a feature may allow for use of intubation device 110 with ETTs and/or stylets of varying lengths and sizes (e.g., pediatric or adult). In some embodiments, such adjustment may be accomplished via control over the drive-down assembly. In other systems, the rail system may be adjusted to accommodate the different sized ETTs. It will be understood that adjustment of swing arm 114 and/or the rail system may be accomplished via any suitable mechanism or combination of mechanisms.

FIG. 12 shows a further example embodiment of a stylet assembly 160 for use with an intubation device and an ETT 162 in accordance with embodiments of the present disclosure. All or part of stylet assembly 160 may be configured to be released, sterilized, cleaned, or otherwise re-used. In other embodiment, all or part of stylet assembly 160 may be configured to be disposed of after use. Stylet assembly 160 comprises stylet body 164. Stylet assembly 160 may be configured such that ETT 162 is oriented over all or part of stylet body 164 and that ETT 162 is limited at one end by stylet arm 166. In some embodiments, stylet arm 166 may comprise one or more couplers (e.g., edge, cavity, and/or tab) configured to temporarily secure, or otherwise interact with, an end of ETT 162 such at that motion of stylet arm 166 may effect motion of ETT 162. In other embodiments, stylet body 164 may be configured to be oriented outside of ETT 162 (e.g., in a side-by-side configuration).

Stylet assembly 160 further comprises stylet tip 168. Tip 168 may comprise one or more sensors (e.g., imaging, chemical, and/or guidance). For example, the tip may include a camera! or other sensory capture device. In some embodiments, the data from said sensors may be utilized to provide feedback to a user of stylet assembly 160 (e.g., through a display device). In other embodiments where the use of stylet assembly 160 is at least partially automated, said data may be utilized by one or more automation mechanisms (e.g., guidance mechanism). While illustrated as being substantially cylindrical, it will be understood that stylet body 164 may comprise any cross-section and that said cross-section may vary along the length of stylet body 164. It will be further understood that stylet body 164 may comprise one or more internal cavities to provide connection to and/or control over tip 168 and sensors thereof.

The tracheal intubation may have two levels for ETT insertion positioning—gross positioning and fine positioning. With use of the ETT delivery system, gross positioning of the ETT may first provide positioning close to the trachea, and additional, precision positioning may be provided via a guidance mechanism and/or a multiple-DOF delivery system, as described herein. The inclusion of the stylet tip provides fine positioning controls in difficult intubation systems.

Stylet arm 166 may be configured to replace an existing arm of an intubation device (e.g., swing arm 114 of FIG. 3 and/or swing arm 146 of FIG. 4). In other embodiments, stylet arm 166 may be configured to couple to one or more elements of the intubation device. Accordingly, assembly 160 may further comprise gears 169. Gears 169 may be configured to couple stylet arm 166 to a drive-down mechanism (e.g., electromechanical device) in order to effect motion of stylet arm 166. In other embodiments where stylet arm 166 comprises a drive-down mechanism, gears 169 may be configured to allow rotation of ETT 162 and/or stylet arm 166 via said electromechanical device.

Stylet body 164 may be made from flexible, semi-flexible or rigid materials. In some embodiments, stylet body 164 may be configured to be in a form similar to intubation stylets known in the art. However, it should be appreciated that stylet body 164 may be formed in other configurations. Stylet body 164 may assume various configurations to facilitate automatic movements based on specific motion mechanisms. For example, stylet body 164 may comprise, in whole or in part, extendable sections and/or retractable sections. Accordingly, in such embodiments, stylet arm 166 may be configured to be substantially fixed and stylet arm 164 may be configured to be inserted into the trachea via a substantially telescoping motion.

In other embodiments, stylet body 164 may comprise, in whole or in part, individual segments (e.g., disks and/or tubes) operatively coupled together (e.g., via guide wires) to provide certain degree of rigidity and flexibility to facilitate desired movements. Such features may enable a snake-like movement of the stylet body 164.

Figure 13:
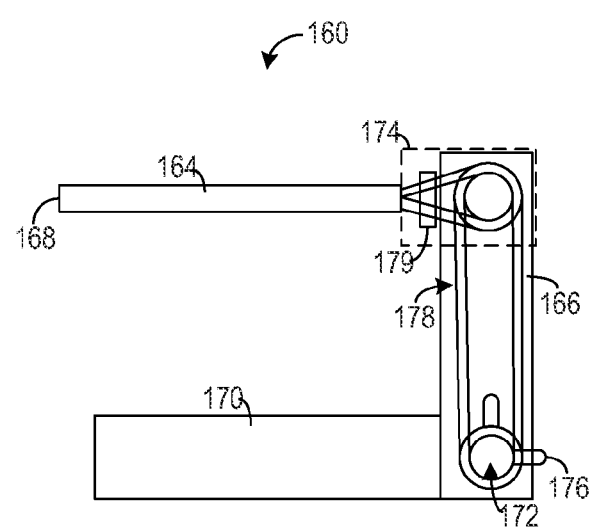
FIG. 13 schematically shows a cross-section view of the stylet assembly of FIG. 12.

FIG. 13 schematically shows a cross-section view of the stylet assembly 160 of FIG. 12. As illustrated, stylet arm 166 may be coupled to handle unit 170 (e.g., handle unit 112 of FIG. 3 and/or handle unit 142 of FIG. 4) at axis 172 such that stylet arm 166 may rotate about axis 172 in a substantially radial path.

As described above in reference to FIG. 12, stylet tip 168 may comprise one or more sensors (e.g., tracheal-specific sensor, also referred to herein as trachea condition sensor) for use in automated and/or manual use case scenarios. Accordingly, stylet assembly 160 may further comprise stylet or borscope module 174. An example stylet module may be configured to provide visual feedback to a user (e.g., via a display device) and/or to one or more guidance mechanisms (e.g., to provide input for pattern matching). As illustrated, borescope module 174 may be integrated, in whole or in part, into stylet arm 166. Borescope module 174 may comprise one or more imaging sensors optically coupled to stylet tip 168 via stylet body 164. Said optical coupling may be accomplished, for example, via a plurality of optical fibers oriented within stylet body 164 and coupled to tip 168 and borescope module 174. In other embodiments, said coupling may be accomplished via one or more optical cladding materials applied to the surface of one or more cavities within stylet body 164. Stylet tip 168, stylet body 164, and/or borescope module 174 may further comprise one or more optical devices (e.g., lenses) configured to augment the performance of the one or more imaging sensors of borescope module 174. It will be understood that these scenarios are presented for purpose of example, and are not intended to be limiting in any manner.

Control over stylet body 164, stylet tip 168 and/or sensors thereof (e.g., sensors of borescope module 174) may be accomplished via one or more input mechanisms 176 (e.g., input device 126 of FIG. 3). Input mechanisms 176 may comprise one or more user-actuatable mechanisms including, but not limited to, joysticks, buttons, knobs, directional pads, touch-sensitive surfaces, and the like. Control may be translated from input mechanisms 176 to stylet tip 68 and/or sensors thereof via one or more mechanical mechanisms.

For example, input mechanism 176 may be coupled to one or more guide wires 178. For example, as described above, guide wires 178 may be operatively coupled to one or more sections (e.g., disks) of stylet body 164 in order to provide telescoping and/or snake-like movement. In other embodiments, guide wires 178 may be configured to provide additional and/or different movement of stylet body 164. Stylet assembly 160 may further comprise one or more guide wire management mechanisms 179 to define motion of guide wires 178. Guide wire mechanisms 179 may include, but are not limited to, grooves, tabs, pulleys, and the like. Mechanisms 179 may be coupled to one or more elements of stylet assembly 160 (e.g., stylet arm 166 and/or stylet body 164).

In other embodiments, input mechanism 176 may be configured to translate user input into one or more representative electrical signals. Accordingly, stylet assembly 160 may comprise one or more electromechanical devices (e.g., motor) to translate said electrical signals into articulation of stylet tip 168 and/or stylet body 164. It should be appreciated that articulation may comprise movement in multiple DOF.

For example, stylet body 164 and/or stylet tip 168 may be configured to perform "up and down movement" referred to as a first DOF, "right and left movement" referred to as a second DOF, and "forward and back movement" referred to as a third DOF. As another example, stylet body 164 and/or stylet tip 168 may articulated in an additional DOF via adjustment of pitch (e.g., incline) and/or yaw (e.g., rotation along major axis of stylet body 164). It will be understood that stylet body 164 and/or stylet tip 168 may be configured to be articulated in fewer, additional, and/or different DOFs without departing from the scope of the present disclosure.

While stylet assembly 160 is described as being configured to be oriented at least partially within, and/or next to, ETT 162, it will be understood that an ETT (e.g., ETT 162) may comprise, in whole or in part, the above-described features of assembly 160. For example, ETT 162 may be configured to provide articulation as described above in reference to stylet body 164. As another example, ETT 162 may comprise one or more described sensors as described herein.

Figure 14:
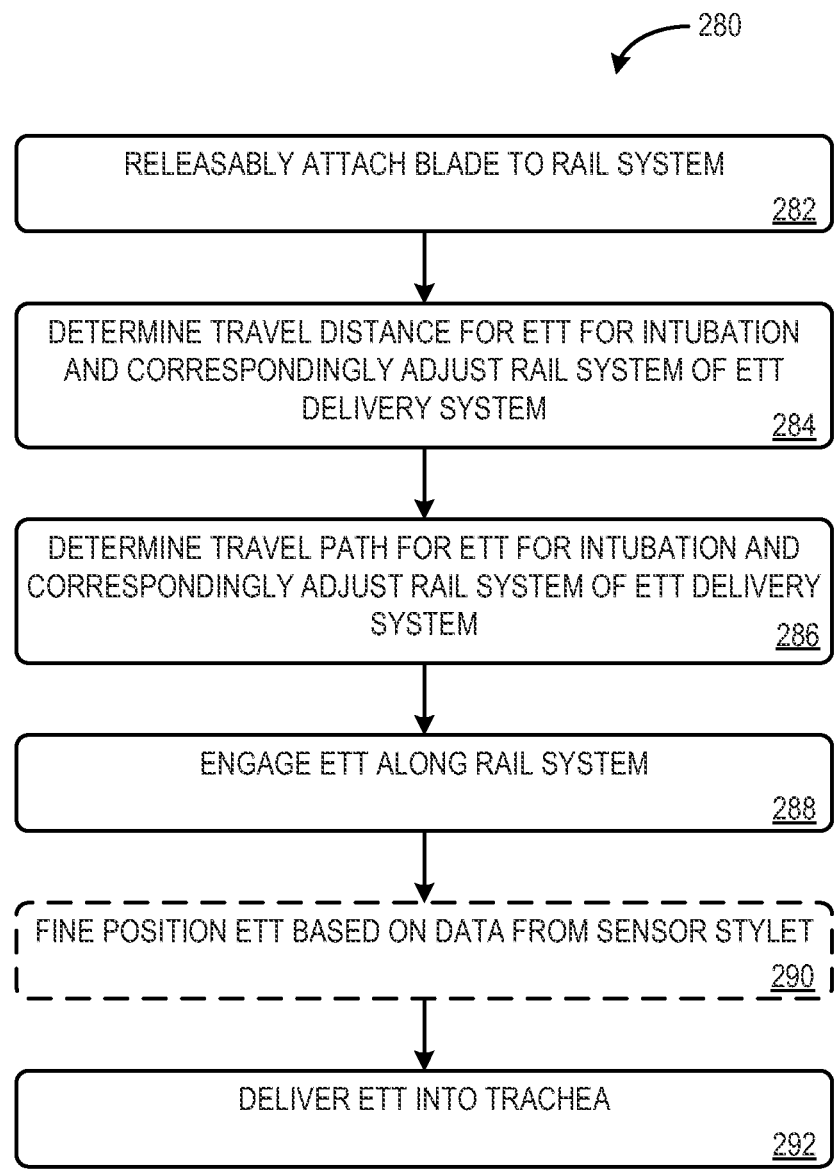
FIG. 14 shows a process flow depicting an embodiment of a method for intubating a patient.

Turning now to FIG. 14, a method 280 is disclosed for intubating a patient in accordance with various embodiments of the present disclosure. At 282, method 280 comprises releasably attaching a blade to a rail system. For example, as described above in reference to FIG. 3, guide rail 118, blade 120, and/or arm stop 122 may form a substantially integrated or unitary unit. In other embodiments such elements may be separated from the remaining elements of intubation device 110 to facilitate sterilization and/or disposal. Attaching the blade to the rail system may utilize one or more mechanisms (e.g., snap-in fittings, grooves, and/or adhesive) of the blade and/or rail system. It should be appreciated that in other embodiments the blade may be fully integrated such that it is or is a part of the rail system. It should be further appreciated that an ETT may be part of a pre-packaged system.

At 284, method 280 comprises determining a travel distance for an ETT for intubation and correspondingly adjusting a rail system of the ETT delivery system. In manual use case scenarios, said determining and adjusting may be performed manually by a user of the intubation device. For example, adjusting may be performed via one or more user-actuatable mechanisms (e.g., adjusters 132 and 134 of FIG. 10). Such adjustments may be based on visual cues and/or sensor or cameral data. In other embodiments, determining and/or adjusting may be accomplished, in whole or in part, via one or more automatic or machine guidance mechanisms.

At 286, method 280 comprises determining a travel path, also referred to as a track, for an ETT for intubation and correspondingly adjusting a rail system of the ETT delivery system. Similar to adjustment of travel distance as described above, adjustment of travel path and track may be accomplished manually and/or via one or more guidance mechanisms.

It should be appreciated that in some embodiments adjusting the rail system may be based on sensor or camera data. For example, sensor data may comprise data from one or more sensors coupled to a stylet tip (e.g., stylet tip 168 of FIG. 12) and/or coupled to the leading edge of a blade (e.g., blade 120 of FIG. 10). The sensor data may be provided to a user via a display device (e.g., display device 258 of FIGS. 9A-B) and/or may be utilized via one or more guidance mechanisms, such as an automatic guidance mechanism. Guidance mechanisms utilizing such sensor data will be discussed in greater detail below. It should be appreciated that in some embodiments, other data may be used to adjust the rail system for intubation.

At 288, method 280 includes engaging an ETT along the rail system. As described above in reference to various embodiments, the intubation device may comprise one or more features (e.g., arm stop 122 of FIG. 1 and tube guides 156 of FIG. 4) configured to engage an ETT. Such features may comprise one or more coupling guides (e.g., tab, clip/locking feature, pressure fitting, and/or adhesive) configured to temporarily couple the ETT to the rail system and/or the blade.

Figure 15:
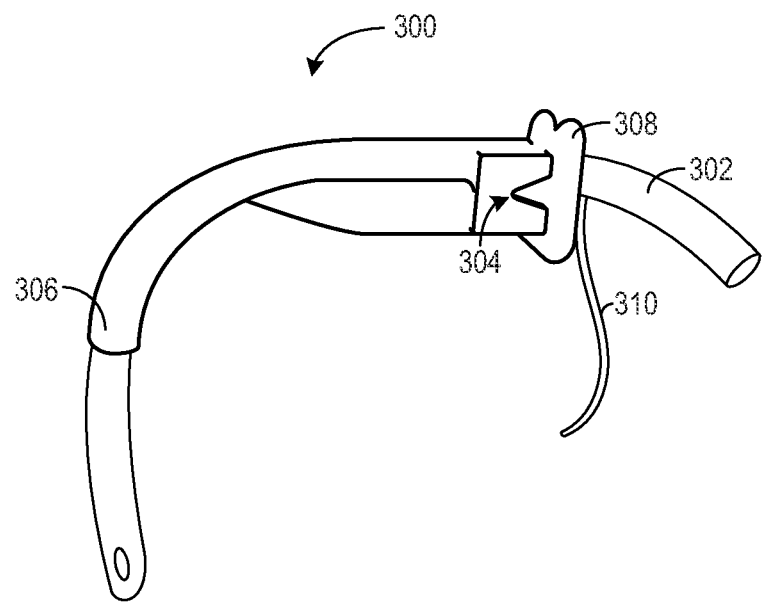
FIG. 15 shows a non-limiting example of a detachable blade assembly in accordance with an embodiment of the present disclosure.

Turning now to FIG. 15, a non-limiting example of a detachable blade assembly 300 with ETT 302 is shown in accordance with an embodiment of the present disclosure. Assembly 300 may be configured to be temporarily coupled to one or more elements of an intubation device (e.g., guide rail 118 and/or blade 120 of FIG. 3) via coupling mechanism 304. Such coupling may allow assembly 300 to temporarily secure ETT 302 and/or to provide functionality similar to a laryngoscope blade. Accordingly, assembly 300 (blade and tube) may be configured to be detachable from an intubation device after assembly 300 has been inserted into the patient's airway. The blade and tube may remain in position during the procedure and removed upon completion of the procedure. The blade and tube may thus be removable from the device, and in some embodiments, disposable as a unit. Such a system may potentially allow for easy sterilization and/or disposal. Additional potential benefits will be discussed in greater detail below.

Coupling mechanism 304 is illustrated as comprising a V-shaped notch into which one or more complimentary features slides, locks, and/or clips into. It will be understood that mechanism 304 may comprise any mechanism or combination of mechanisms configured to temporarily couple assembly 300 to an intubation device without departing from the scope of the present disclosure.

Assembly 300 comprises a substantially unitary housing comprising coupling mechanism 304, blade 306, and mouth guard 308. Assembly 300 may be configured to be inserted into a patients airway such that blade 306 is inserted first. Assembly 300 may be further configured to be inserted until mouth guard 308 is aligned with the patient's teeth and/or lips. Accordingly, assembly 300 may be configured to prevent a patient from biting down during intubation, and thus may decrease the likelihood of choking or other airway-blocking event. When assembly 300 is detached from the rest of an intubation device, assembly 300 may be further configured to provide secure, proper positioning of ETT 302 within the trachea without additional mechanisms (e.g., tape).

In order to facilitate removal, assembly 300 further comprises removal mechanism 310. Removal mechanism 310 may be coupled to any part of assembly 300 via any suitable mechanism or combination of mechanisms (e.g., adhesive, eyelet, etc.).

Returning to FIG. 14, method 280 may optionally include, at 290, fine positioning the ETT based on a data from a sensor stylet (e.g., stylet assembly 160 of FIG. 12). In some embodiments, said data may be provided to a user via a display device for manual fine positioning of the ETT. In other embodiments, said data may be utilized by one or more guidance mechanisms to provide automated fine positioning. Such guidance mechanisms will be discussed in greater detail below.

At 292, method 280 comprises delivering the ETT into the trachea. The ETT may be delivered via a delivery mechanism, such as swing arm 114 of FIG. 3. In some embodiments, the delivery mechanism may be coupled to an electro-mechanical device (e.g., a motor) to effect motion of the delivery mechanism. In other embodiments, the delivery mechanism may be user-actuatable (e.g., by applying pressure to the free end of swing arm 114 of FIG. 1).

It should be appreciated that in some embodiments, the blade may be detachably coupled to the rail system. The blade may be detachably coupled for sterilization purposes. However, in some embodiments, the blade may also be configured to be releasably locked to the ETT. In such examples, the blade and the ETT may be decoupled from the rail system when the ETT is delivered into the trachea. For example, the blade may be releasably attached to the ETT upon detaching from the rail system. Decoupling of the blade from the rail system enables the temporary delivery of both the ETT and the blade. The blade may then remain coupled with the ETT during use such that the two are removed together. Removal of the ETT results in removal of the blade. In other embodiments, the blade may be selectively removed from the ETT during or after use of the ETT.

As discussed above, various embodiments of the present disclosure may comprise one or more sensors (e.g., imaging, tracheal-specific, chemical). For example, sensors may detect existing trachea conditions, detect introduced trachea conditions, and/or may detect signal trachea conditions. Alternatively, selected sensors may detect the same trachea condition at different levels. For example, the sensors may comprise $CO_2$ sensors that detect $CO_2$ at different concentration levels. Sensors may further comprise a pressure sensor, a flow rate sensor, and/or a light sensor.

Trachea conditions may include any identifiable characteristic that differentiates the trachea from the esophagus because the characteristic is either only present in the trachea or is present in different magnitudes or patterns in the trachea and the esophagus. Example trachea conditions may include, but are not limited to $CO_2$, oxygen ($O_2$), nitrogen ($N_2$), helium, air flow, positive or negative pressure, pressure change, air flow, inhalation anesthetics (e.g., desflurane, isoflurane, sevoflurane), Xenon, nitrous oxide ($N_2O$), sound including ultrasound, alcohol, isotope, light, magnet, temperature, and electricity, etc.

The existing trachea condition may include characteristics naturally existing in the trachea. In some embodiments, the existing trachea condition may be considered as natural trachea condition. For example, $CO_2$ is exhaled from the lungs and is naturally present in the trachea but is absent from the esophagus. Thus, the trachea condition may be $CO_2$ and a trachea condition sensor may be a $CO_2$ sensor configured to detect the presence of $CO_2$. In some embodiments, the $CO_2$ sensor may be configured to detect $CO_2$ concentrations at or above an atmospheric level. It should be appreciated that the $CO_2$ sensor may be any suitable $CO_2$ sensor that can detect $CO_2$ qualitatively or quantitatively and can respond to the $CO_2$ concentration variations or $CO_2$ gradients quickly.

Similarly, oxygen and nitrogen exist naturally in the trachea. Thus, the trachea condition may be oxygen or nitrogen and the trachea sensor may be an oxygen sensor or a nitrogen sensor.

In another example, air flow in the trachea may be a unique identifier of the trachea to distinguish the trachea from the esophagus. The trachea condition may be airflow and air pressure. The trachea condition sensor may be a flow rate meter that measures air movement or amount of air in the trachea. The trachea condition sensor may also be a pressure sensor that measures the pressure or pressure changes in the trachea. In some embodiments, as an example, an automatic intubation device for a spontaneous ventilation patient may be configured in such a manner that a patient's respiratory movement initiates and guides the insertion of the ETT (e.g., via stylet assembly 160 of FIG. 12) in response to an intensified signal from air flow or pressure sensors. It should be noted that an air flow rate meter and a pressure sensor may be any suitable sensor that can detect the desired levels of air flow and air pressure (either positive or negative pressure).

As another example, air temperature may be a unique identifier of the trachea. Inhalation temperature is typically near room temperature (e.g., 20° C. in Operating Room), while exhalation temperature is typically near body temperature (e.g., 35° C.). A thermal sensor (e.g., night-vision camera) may be configured to detect temperature differences as low as 0.1° C. Accordingly, a thermal image sensor may be utilized to detect a temperature difference in order to further guide insertion of an ETT. The thermal image sensor may be used alone or in combination with other sensors in defining the ETT delivery path.

In yet another example, an existing trachea condition may be sound in the trachea generated by the air movement, air turbulence and phonation (vocal cord is the beginning of the trachea). Thus, any suitable sound sensor may be used as a trachea condition sensor.

In addition, the trachea condition may be an introduced or artificial condition foreign to the trachea. For example, a compound or a tracer may be introduced into the patient by inhalation, digestion or injection. Exhaling the compound or the tracer from the lungs may create a trachea-specific condition. As an example, the compound may include intravenous alcohol, helium, inhalation anesthetics, Xenon, or $N_2O$, etc. The trachea condition sensor or compound detecting sensor may include a sensor to detect the presence and concentration of one or more such compounds or tracers.

In another example, an introduced compound may be spiked with a trace amount of an isotope, such as $H_3O$. The isotope may be detected by an isotope sensor.

It should be noted that the introduced tracer may be any suitable compound or substance that can be introduced to the patient and its presence in the trachea or around the entry point to the trachea is detectable by a sensor. The substance may be in a state of gas, liquid, or solid. The compound may have minimum side effect to the patient.

In addition to the existing and introduced trachea conditions, a third type of trachea condition may be a signal trachea condition. In some embodiments, the signal trachea condition may be a detectable signal or trachea identifier generated by a trachea identifier source. Such a source may be coupled to the leading edge of a laryngoscope blade (e.g., blade 120 of FIG. 3) and/or to a stylet tip (e.g., stylet tip 168 of FIG. 12).

Because of different anatomical locations of the trachea and esophagus (trachea 24 is located anterior to esophagus 32 as shown in FIG. 1) and different geometric structures around entries to the trachea and the esophagus (the trachea is an open tube-like cartilage structure verse esophagus which is normally collapsed in the absence of swallowing). The signal transmitted to the trachea or around the trachea may have different intensities or patterns than those in the esophagus. Thus, detected signal may provide information that distinguishes the trachea from the esophagus. In some embodiments, the trachea identifier may be in a form of energy. In one example, the trachea identifier source may be a light source. Such a trachea identifier source may be configured to generate any suitable light, such as visible light, ultraviolet, infrared, laser, etc. The trachea identifier source may also include light emitting diodes (LEDs). The trachea condition sensor may be a light sensor.

In another example, the trachea identifier source may include a sound device to generate sound. The sound device may be configured to create and send sound in any suitable decibel level to the trachea. For example, the sound may be audible sound and ultrasound. The trachea condition sensor may be a sound homing detector.

In yet another example, the trachea identifier source may comprise a magnetic source configured to generate a magnetic field in the trachea. The magnetic source may include any suitable source, such as a permanent magnet or electric magnet. The trachea sensor may be a magnetic sensor.

In still another example, an electrode pair may generate a detectable electric signal. For example, the trachea identifier source may include a first electrode that forms an electrical cell together with a second electrode disposed on a stylet (e.g., stylet body 164 of FIG. 12). An electrical signal may be generated when both first electrode and second electrode are in contact with the patient's body. A specific range of electrical impedance may exist when the stylet contacts the trachea. The range may distinguish the trachea from the esophagus. Thus, it is possible to identify the trachea by a measurement of electric signals, such as a voltage or a current generated in the cell. It should be appreciated that, in some embodiments, the first electrode may be employed as a trachea condition sensor.

It will be understood that the above-described sensors are presented for the purpose of example, and are not intended to be limiting in any manner.

Furthermore, as described above, various embodiments of the present disclosure may comprise one or more guidance mechanisms. Such guidance mechanisms may be configured to utilize data from one or more of the above-described sensors. For example, the guidance mechanisms may be configured to perform pattern recognition and/or pattern matching.

The pattern matching and the pattern recognition may enable identification of the topographic features that cannot be observed by human eyes or cannot be identified correctly by human eyes via a direct video image under some clinical conditions. The guidance mechanisms may be configured to identify one or more topographical features and select the identifiable topographical features to determine the topographical pattern indicating the trachea opening. Trachea identification based on analysis of selected topographical features allows the trachea identification under some clinical conditions where some topographical features are not identifiable due to abnormality or trauma of the epiglottis, the vocal cords, etc. In this way, such guidance mechanisms may provide accurate and fast identification of the trachea and may therefore increase the success rate of the intubation in various clinical situations.

The guidance systems may be configured to analyze data from one or more imaging sensors for the presence of the topographical features. The topographical features include the configuration of the vocal cords, such as an inverted "V" shape at rest, distinguished white color, vibrated folds of the vocal cords at phonation and the dynamic thermal image changes during a respiratory cycle. The topographical features further include structures surrounding the vocal cords, such as the shape of the epiglottis and arytenoids cartilages, and the esophagus opening as well as the vocal cords' spatial relationship and the vocal cords' relative color to its surrounding structures. In some embodiments, the topographical features of the vocal cords may be used alone to identify the vocal cords or the trachea opening. In other embodiments, the topographical features of the vocal cords may be used as a major identifier, and other topographical features surrounding the vocal cords and their relationship may be used as additional identifiers to confirm the trachea opening identification.

The topographical pattern indicating the trachea opening may be identified using any appropriate data processing technologies that identify a pattern based on the specific features. For example, the image data may be analyzed using pattern matching that checks for the presence of the constituents or features of a given pattern. For example, the image data may be analyzed for the presence of the topographic features by comparing a predetermined pattern. The predetermined pattern may be a specific topographical pattern for adults or a specific topographical pattern for children. Additionally, the pattern matching may include a comparison with a predetermined pattern for patients with an abnormal airway.

Pattern matching may include checking the presence of one or more of the topographical features in the captured sensor data (e.g., image data). In one example, it may be determined that the topographical pattern indicating the trachea opening is present if the captured image data include features matching the structural features of the vocal cords and/or epiglottis. In another example, it may be determined that the topographical pattern indicating the trachea opening is present if the captured image data include features matching the features of the vocal cord folds vibration or the motion in the trachea opening during phonation. Based on the analysis of the topographical pattern, the navigation guidance may be generated to direct the movement of the guide stylet (e.g., stylet body 164 of FIG. 12). It should be appreciated that the navigation guidance may be generated if any single topographical feature matches with the predetermined pattern or if two or more topographical features match with the predetermined pattern. Further, it should be appreciated that any appropriate mathematic models can be used for pattern matching.

In some embodiments, the image data may be analyzed using pattern recognition based on the categories of the pattern. The pattern recognition technique may include collecting data, extracting features (e.g., numeric or symbolic information from the data) from the collected data and classing/categorizing the data based on the extracted features. Any appropriate pattern recognition technique can be used for the pattern recognition. In one example, the pattern recognition may be based on a prior knowledge via supervised learning. That is, the classification may be based on a set of classified or described patterns called the training set. In another example, the pattern recognition may establish the classes based on statistical regularities of the pattern, i.e., unsupervised learning. The guidance mechanism may be configured to store one or more sets of classified patterns with the topographic features and perform the pattern recognition via the supervised learning. Alternatively or additionally, the guidance mechanism may perform the pattern recognition based on a statistical model of the topographic features via unsupervised learning. Again, the topographic features may be one or more of the topographic features of the trachea, the esophagus and their surrounding, and the trachea identification may be based on recognition of one or more of the topographic features. The navigation guidance may be generated based on the pattern recognition. It should be appreciated that any appropriate mathematic models or algorithms can be used for pattern recognition.

In some embodiments, guidance mechanism may be configured to track a position of the guide stylet via an image corresponding to the position. In one example, the guidance mechanism may include a predetermined map with a relationship between the airway images and positions of the guide stylet. As such, during the intubation, a current position of the guide stylet relative to the trachea opening (e.g., up, down, right or left relative to the trachea opening) may be determined by comparing the captured image with the predetermined map.

Again, as pattern recognition is conducted on a significant amount of real time data for the regularities or classification, pattern recognition may enable identification of the topographic features that cannot be observed by human eyes. The features identifiable by the pattern recognition are referred to as the machine recognizable features. Further, the identification of one or more machine recognizable features as opposed to the observation on an overall visualization of an image allows the correct trachea identification under the clinical conditions where an intubation is not possible by a direct view or a video image.

It should be appreciated that any suitable data processing may be used to analyze the topographical pattern indicating the trachea opening. For example, the guidance mechanism may comprise a module or an algorithm to recreate an image based on the captured image data. For example, an indiscernible topographical feature from a captured video image may be enhanced on a processed image once the feature is identified by the image reconstruction module. Alternatively, a missing topographical feature in the captured image may be superimposed into the processed image so that the trachea opening can be identified. The processed image can be displayed to a user via a display device in order to improve the visualization of the trachea opening.

Figure 16:
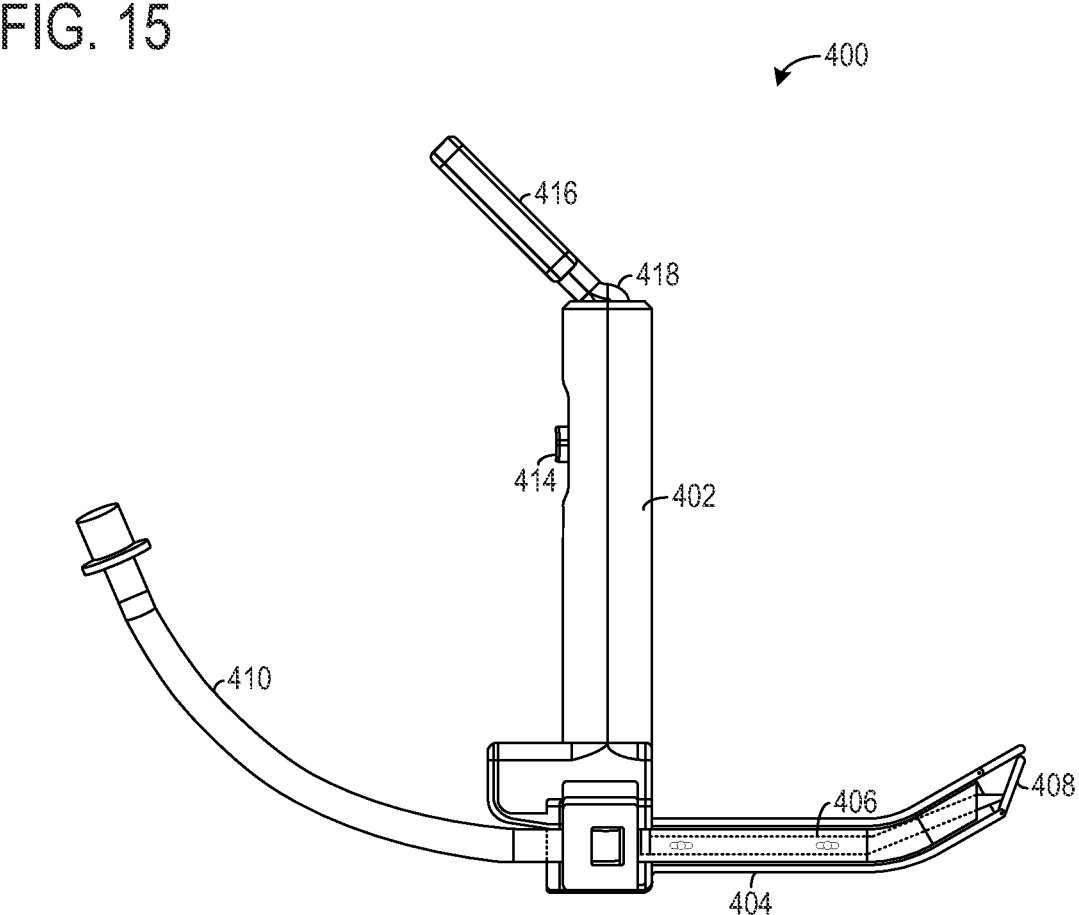
FIGS. 16-23 provide a further example of an ETT delivery system.

Referring now to the final figures, FIGS. 16-23 provide a further non-limiting illustration of an example ETT delivery system. Turning to FIG. 16, a side view of intubation device 400 is shown. As an example, intubation device 400 comprises handle unit 402 coupled to guide assembly 404. Guide assembly 404 comprises linkage 406 coupled to lip 408 to provide adjustment of lip 408. The position of lip 408 may be configured to at least partially guide the motion of ETT 410 as ETT 410 moves through guide assembly 404 (e.g., via interaction with a roller and/or other mechanisms). Handle unit 402 comprises user-actuatable input mechanism 412 (e.g., button, knob, joystick, etc.) electrically and/or mechanically coupled to linkage 406 in order to provide adjustment of lip 408. Input mechanism 412 may be further coupled or linked to effect motion of a device, such as a roller, in order to effect motion of ETT 410.

Intubation device 400 further may comprise display device 416 coupled to handle unit 402 via any suitable coupling device, such as a ball joint 418. In other embodiments, display device 416 may be coupled to handle unit 402 via other mechanisms and/or may be detachable from handle unit 402. Display device 416 may be configured to display information received from one or more sensors and/or cameras to assist with placement of ETT 410 into the patient's airway.

Figure 18:
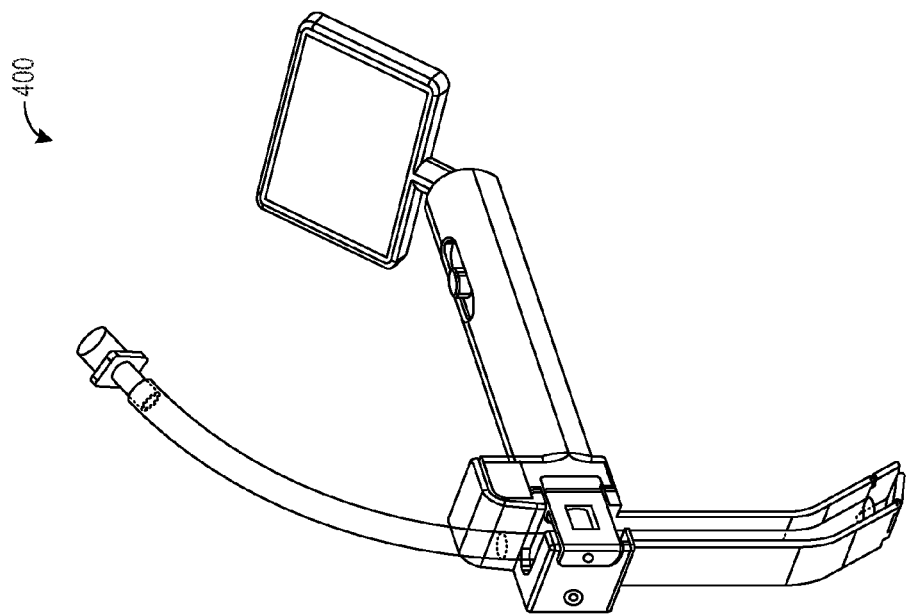
Figure 17:
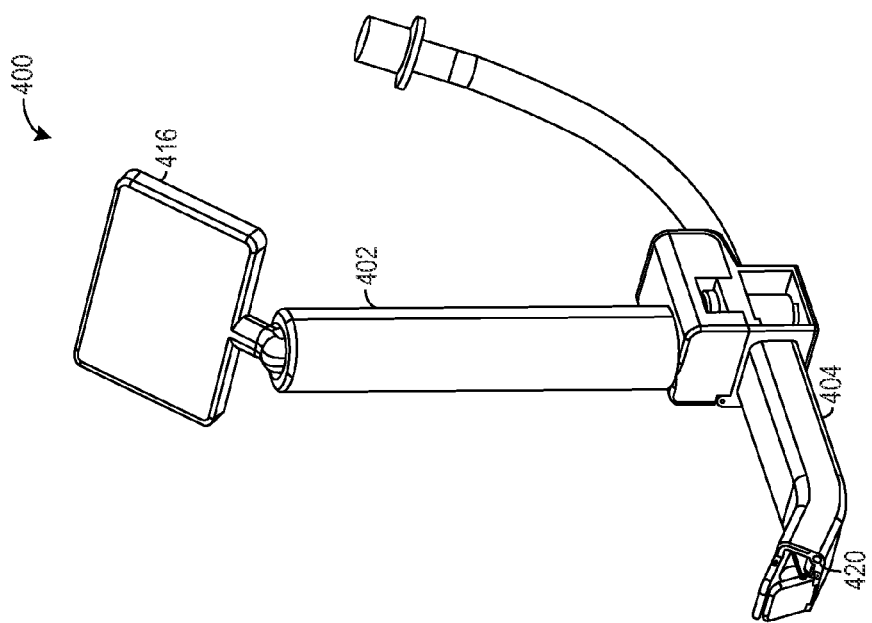

FIGS. 17 and 18 show perspective views of intubation device 400. As illustrated in FIG. 17, guide assembly 404 further may comprise a light guide 420. Light guide 420 may be configured to direct light into an internal imaging sensor of handle unit 402 to provide feedback via display device 416.

Figure 20:
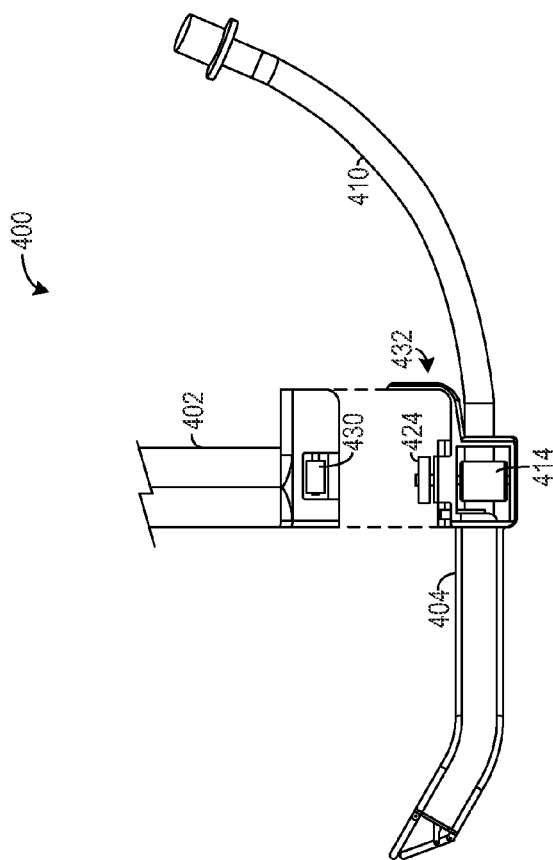
Figure 19:
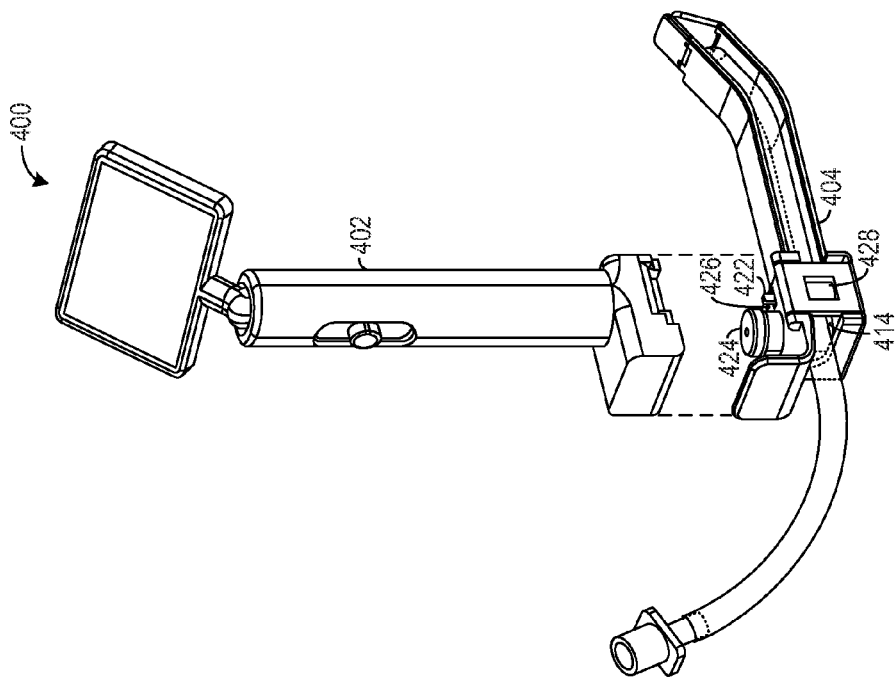

FIGS. 19 and 20 show an example handle unit 402 detached from guide assembly 404. Such detachability may allow for easy sterilization and/or disposal of guide assembly 404 and/or handle unit 402. Specifically, FIG. 19 illustrates lip coupler 422, roller coupler 424, and optical coupler 426 of guide assembly 404. Lip coupler 422 is coupled to linkage 406 (not illustrated), roller coupler 424 is coupled to roller 414 and/or roller 428, and optical coupler is coupled to light guide 420 (not illustrated). Optical coupler 420 may be configured to couple light guide 420 to an imaging sensor located within handle unit 402. Couplers 422 and 424 may be configured to couple one or more actuators (e.g., input mechanism 412 and/or electromechanical mechanism controlled thereby) of handle unit 402 to roller 414 and linkage 406 (not illustrated), respectively.

FIG. 20 further illustrates an example mechanical coupling between handle unit 402 and guide assembly 404 of intubation device 400. As shown, handle unit 402 comprises gear 430 (e.g., worm drive gear) configured to interact with roller coupler 424 in order to effect rotation of roller 414, and thus motion of ETT 410, when handle unit 402 is coupled to guide assembly 404. Handle unit 402 may therefore comprise one or more mechanisms (e.g., electromechanical actuator) configured to effect rotation of gear 430.

FIG. 20 further shows edge 432. Edge 432 may comprise one or more features (e.g., groove, span-in mechanism, etc.) configured to couple guide assembly 404 to handle unit 402. Further, edge 432 may be configured, as illustrated, such that ETT 410 does not contact handle unit 402 during use, and may thus protect handle unit 402 from bodily fluids. Edge 432 may therefore increase the lifespan of handle unit 402 and/or may ensure handle unit 402 remains sanitary.

Figure 21:
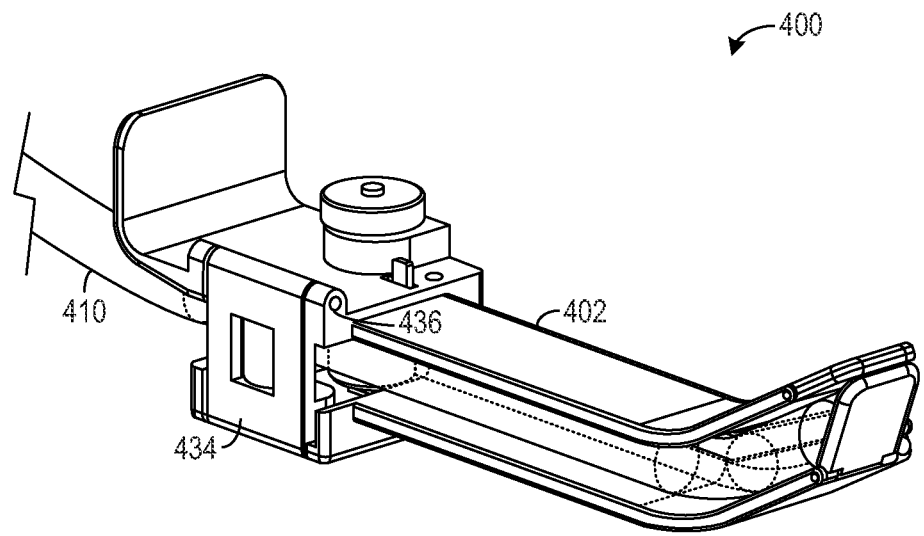
Figure 22:
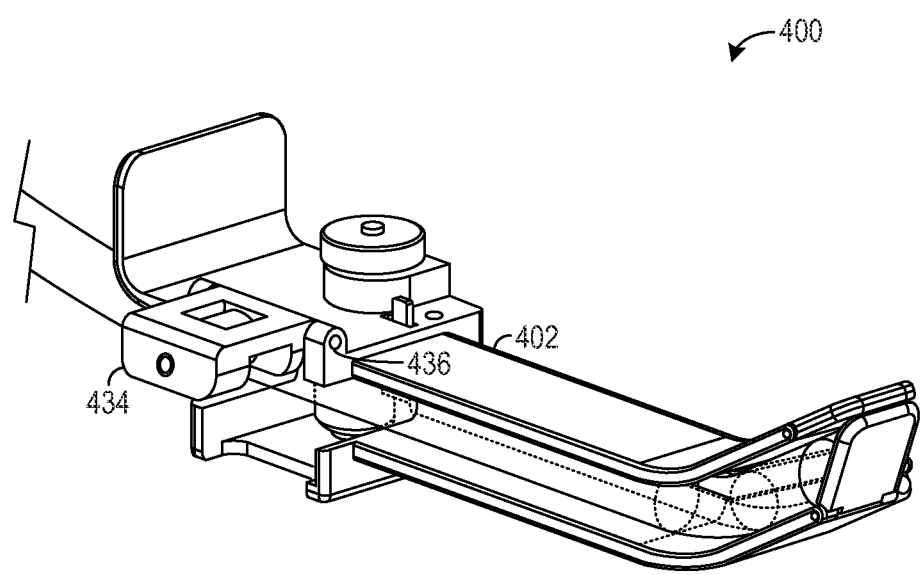

FIGS. 21 and 22 show guide assembly 404 of intubation device 400. FIG. 21 illustrates guide assembly 404 in the use position. Guide assembly 404 further comprises access assembly 434 to provide easy coupling of ETT 410 to guide assembly 404. Access assembly 434 may be coupled to handle unit 402 at axis 436 such that access assembly 434 may pivot about said axis to allow insertion of ETT 410. Access assembly 434 may be user-actuatable and/or may be actuatable via one or more other mechanisms (e.g., electromechanical actuator).

FIG. 22 shows access assembly 434 with access assembly 434 in the "loading" position (i.e., rotated upwards about axis 436).

Figure 23:
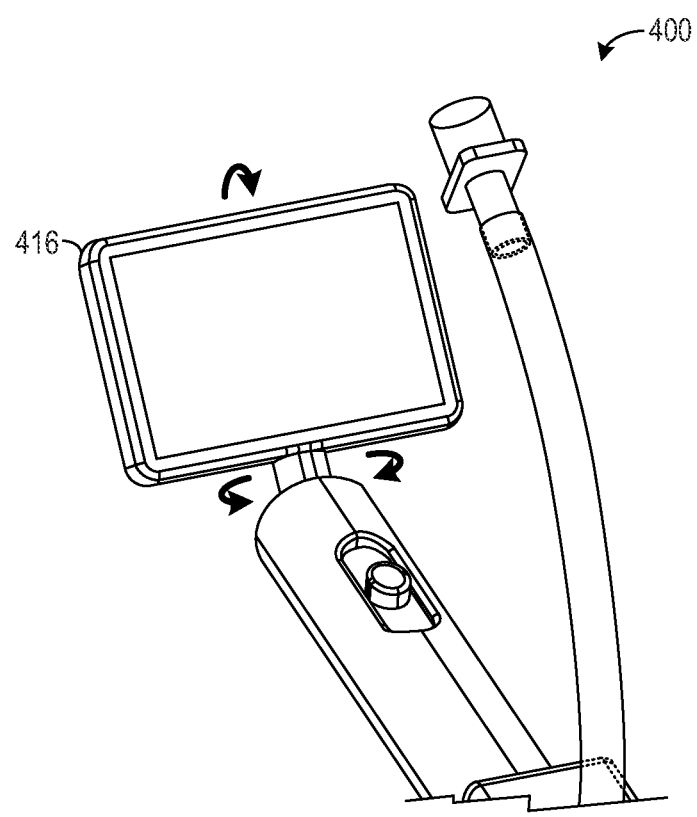

FIG. 23 shows adjustment of display device 416 via ball joint 418 (not illustrated). In other embodiments, display device 416 may be adjustable along different and/or additional degrees of freedom.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An ETT delivery system for delivery of an ETT into a trachea, comprising:
   an integrated rail system to deliver the ETT;
   an ETT steering mechanism that comprises at least one degree of freedom (DOF);
   a disposable blade coupled to the rail system, wherein the disposable blade is detachably coupled to the rail system and wherein the disposable blade is configured to releasably lock to the ETT after being decoupled from the rail system;
a driving mechanism that drives the ETT along the rail system and follows a direction of the steering mechanism; and
a delivery mechanism operatively linked with the integrated rail system to deliver the ETT into the trachea.

2. The ETT delivery system of claim 1, wherein the ETT steering mechanism includes an active lip and a passive lip positioned on the disposable blade that are configured to adjust an ETT tip direction and to move simultaneously in the same direction.

3. The ETT delivery system of claim 1, wherein the rail system comprises a guide mechanism.

4. The ETT delivery system of claim 1, wherein the rail system defines a delivery path and is configured for the ETT to move along the delivery path.

5. The ETT delivery system of claim 1, wherein the delivery mechanism comprises one or more rollers.

6. The ETT delivery system of claim 1, wherein the delivery mechanism is configured to effect motion of the ETT.

7. The ETT delivery system of claim 1, further comprising a stylet to provide additional definition of an ETT delivery path.

8. The ETT delivery system of claim 7, wherein the stylet includes one or more trachea condition sensors.

9. The ETT delivery system of claim 1, wherein a positioner is operatively linked with the rail system to enable movement in one or more degrees of freedom in positioning the ETT.

10. The ETT delivery system of claim 1, wherein the rail system is configured to control travel distance and travel path of the ETT.

11. The ETT delivery system of claim 1, further comprising a sensor stylet for fine guidance of the ETT.

* * * * *

UNITED STATES PATENT AND TRADEMARK OFFICE
CERTIFICATE OF CORRECTION

PATENT NO. : 9,795,753 B2
APPLICATION NO. : 13/414590
DATED : October 24, 2017
INVENTOR(S) : Chunyuan Qiu Page 1 of 1

It is certified that error appears in the above-identified patent and that said Letters Patent is hereby corrected as shown below:

On the Title Page

In the Related U.S. Application Data section:
Item (63) correct "Apr. 21, 2012" to read "Apr. 21, 2010".

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*